US009957697B2

(12) United States Patent
Taylor et al.

(10) Patent No.: US 9,957,697 B2
(45) Date of Patent: May 1, 2018

(54) SYSTEMS AND METHODS FOR CONTROLLING FLUSHING APPARATUS AND RELATED INTERFACES

(71) Applicant: Mueller International, LLC, Atlanta, GA (US)

(72) Inventors: Thomas Moriz Taylor, Naples, FL (US); Harold Thomas Mosley, Fort Myers, FL (US)

(73) Assignee: Mueller International, LLC, Atlanta, GA (US)

( * ) Notice: Subject to any disclaimer, the term of this patent is extended or adjusted under 35 U.S.C. 154(b) by 279 days.

(21) Appl. No.: 14/858,463

(22) Filed: Sep. 18, 2015

(65) Prior Publication Data
US 2016/0010315 A1 Jan. 14, 2016

Related U.S. Application Data

(63) Continuation of application No. 13/117,963, filed on May 27, 2011, now Pat. No. 9,151,023.

(51) Int. Cl.
E03B 7/08 (2006.01)
G01N 33/18 (2006.01)
C02F 1/00 (2006.01)
G01N 1/20 (2006.01)
(Continued)

(52) U.S. Cl.
CPC ............... *E03B 7/08* (2013.01); *C02F 1/006* (2013.01); *G01N 1/20* (2013.01); *G01N 33/18* (2013.01); *G01N 33/1826* (2013.01); *G05B 19/05* (2013.01); *G05D 7/0635* (2013.01); *C02F 1/008* (2013.01); *C02F 2209/006* (2013.01);
(Continued)

(58) Field of Classification Search
None
See application file for complete search history.

(56) References Cited

U.S. PATENT DOCUMENTS 1,018,251 A 2/1912 McKee
1,086,841 A 2/1914 Mueller
RE21,470 E 5/1940 White
(Continued)

FOREIGN PATENT DOCUMENTS

AU 2011202554 12/2012
AU 2015201277 10/2017
(Continued)

OTHER PUBLICATIONS

Taylor, Thomas M.; Australian Patent Examination Report for Serial No. 2015201277, filed Jun. 1, 2011, dated Nov. 22, 2016, 5 pgs.
(Continued)

Primary Examiner — Carlos Ortiz Rodriguez
(74) Attorney, Agent, or Firm — Taylor English Duma LLP

(57) ABSTRACT

The present disclosure relates to maintaining water quality in a water distribution by controlling a flushing apparatus. In one example implementation, a flushing apparatus performs steps comprising flushing the water distribution system in accordance with a residual flush program, flushing the water distribution system in accordance with a turbidity flush program, flushing the water distribution system in accordance with a pH flush program, and flushing the water distribution system in accordance with a time-based flushing program.

20 Claims, 13 Drawing Sheets

(51) Int. Cl.
*G05B 19/05* (2006.01)
*G05D 7/06* (2006.01)

(52) U.S. Cl.
CPC ... *C02F 2209/008* (2013.01); *Y10T 137/0324* (2015.04); *Y10T 137/86389* (2015.04)

(56) References Cited

U.S. PATENT DOCUMENTS

| | | |
|---|---|---|
| 2,752,307 A | 6/1956 | Baran et al. |
| 2,931,382 A | 4/1960 | Cirillo |
| 3,095,893 A | 7/1963 | Martin |
| 3,103,946 A | 9/1963 | Troxell |
| 3,283,776 A | 11/1966 | Flanagan et al. |
| 3,391,790 A | 7/1968 | Lerner |
| 3,592,212 A | 7/1971 | Schleimer et al. |
| 3,682,311 A | 8/1972 | Bishop |
| 3,962,733 A | 6/1976 | Parry |
| 3,980,096 A | 9/1976 | Ellis et al. |
| 3,993,561 A | 11/1976 | Swearingen |
| 4,002,566 A | 1/1977 | Smith |
| 4,083,377 A | 4/1978 | Luckenbill |
| 4,154,259 A | 5/1979 | Ellis et al. |
| 4,165,532 A | 8/1979 | Kendall et al. |
| 4,182,361 A | 1/1980 | Oakey |
| 4,189,776 A | 2/1980 | Kendall |
| 4,212,424 A | 7/1980 | Fortune |
| 4,216,185 A | 8/1980 | Hopkins |
| RE31,023 E | 9/1982 | Hall, III |
| 4,373,838 A | 2/1983 | Foreman et al. |
| 4,393,891 A | 7/1983 | Snoek et al. |
| 4,483,189 A | 11/1984 | Seal |
| 4,556,080 A | 12/1985 | Picaud |
| 4,575,130 A | 3/1986 | Pemberton et al. |
| 4,584,106 A | 4/1986 | Held |
| 4,615,390 A | 10/1986 | Lucas et al. |
| 4,639,718 A | 1/1987 | Gasper |
| 4,653,521 A | 3/1987 | Fillman |
| 4,676,914 A | 6/1987 | Mills et al. |
| 4,721,408 A | 1/1988 | Hewlett |
| 4,756,479 A | 7/1988 | Lazenby, III |
| 4,774,978 A | 10/1988 | Lepine, Jr. et al. |
| 4,779,142 A | 10/1988 | Freeman et al. |
| 4,816,154 A | 3/1989 | Hartley et al. |
| 4,830,757 A * | 5/1989 | Lynch .................. G01N 33/18 210/104 |
| 4,838,485 A | 6/1989 | Rinkewich |
| 4,876,530 A | 10/1989 | Hill et al. |
| 4,898,107 A | 2/1990 | Dickinson |
| 4,992,380 A | 2/1991 | Moriarty et al. |
| 5,002,428 A | 3/1991 | Shettel |
| 1,282,298 A | 4/1991 | Franklin |
| 5,010,912 A | 4/1991 | Riding |
| 5,011,598 A | 4/1991 | Nathanson |
| 5,025,754 A | 6/1991 | Plyler |
| 5,032,290 A | 7/1991 | Yamagata et al. |
| 5,042,524 A | 8/1991 | Lund |
| RE33,723 E | 10/1991 | Hartley |
| 5,115,833 A | 5/1992 | Himle |
| 5,133,622 A | 7/1992 | Hewlett |
| 5,136,983 A | 8/1992 | Hostetler et al. |
| 5,176,165 A | 1/1993 | Traylor |
| 5,184,571 A | 2/1993 | Hostetler et al. |
| 5,201,338 A | 4/1993 | McKeague |
| 5,227,067 A | 7/1993 | Runyon |
| 5,227,068 A | 7/1993 | Runyon |
| 5,240,179 A | 8/1993 | Drinkwater |
| 5,249,745 A | 10/1993 | Bertolotti |
| 5,261,348 A | 11/1993 | Neihaus et al. |
| 5,264,368 A | 11/1993 | Clarke et al. |
| 5,291,207 A | 3/1994 | Kikuchi et al. |
| 5,314,619 A | 5/1994 | Runyon |
| 5,324,665 A | 6/1994 | Lessard |
| 5,331,694 A | 7/1994 | Mackenzie et al. |
| 5,332,494 A | 7/1994 | Eden et al. |
| 5,351,712 A | 10/1994 | Houlihan |
| 5,360,488 A | 11/1994 | Hieatt et al. |
| 5,368,227 A | 11/1994 | McGinnis |
| 5,368,343 A | 11/1994 | Allen |
| 5,427,748 A | 6/1995 | Wiedrich et al. |
| 5,479,338 A | 12/1995 | Ericksen et al. |
| 5,480,562 A | 1/1996 | Lemelson |
| 5,490,561 A | 2/1996 | Cardoso-Neto et al. |
| 5,527,470 A | 6/1996 | Suda |
| 5,535,984 A | 7/1996 | Anderson et al. |
| 5,540,845 A | 7/1996 | Blanchard et al. |
| 5,549,133 A | 8/1996 | Sigelakis |
| 5,553,637 A | 9/1996 | Hoeptner, III |
| 5,582,440 A | 12/1996 | Pascaru |
| 5,587,055 A | 12/1996 | Hartman et al. |
| 5,609,124 A | 3/1997 | Leclerc |
| 5,623,900 A | 4/1997 | Topfer et al. |
| 5,623,990 A | 4/1997 | Pirkle |
| 5,645,011 A | 7/1997 | Winkler et al. |
| 5,746,923 A | 5/1998 | Forward |
| 5,775,372 A | 7/1998 | Houlihan |
| 5,797,417 A | 8/1998 | DeLattre et al. |
| 5,803,111 A | 9/1998 | Soszka |
| 5,813,363 A | 9/1998 | Snelling |
| 5,817,231 A | 10/1998 | Souza |
| 5,829,475 A | 11/1998 | Acker |
| 5,865,991 A | 2/1999 | Hsu |
| 5,885,364 A | 3/1999 | Hieatt et al. |
| 5,915,395 A | 6/1999 | Smith |
| 5,921,207 A | 7/1999 | DiSalvo et al. |
| 5,921,270 A | 7/1999 | McCarty |
| 5,979,482 A | 11/1999 | Scott |
| 5,996,608 A | 12/1999 | Hunter et al. |
| 6,003,780 A | 12/1999 | Gurries, II et al. |
| 6,021,664 A | 2/2000 | Granato et al. |
| 6,035,704 A | 3/2000 | Newman |
| 6,044,911 A | 4/2000 | Haase, III |
| 6,056,211 A | 5/2000 | DiLoreto |
| 6,062,259 A | 5/2000 | Poirier |
| 6,062,606 A | 5/2000 | Carpini |
| 6,063,275 A | 5/2000 | Traylor |
| 6,095,429 A | 8/2000 | Killgrove et al. |
| 6,116,525 A | 9/2000 | Grimes |
| 6,170,514 B1 | 1/2001 | Esmailzadeh |
| 6,221,257 B1 | 4/2001 | Grim |
| 6,227,463 B1 | 5/2001 | Porter |
| 6,227,464 B1 | 5/2001 | Allmendinger et al. |
| 6,290,267 B1 | 9/2001 | Swingley |
| 6,294,096 B1 | 9/2001 | Pate |
| 6,358,408 B1 | 3/2002 | Newman |
| 6,385,794 B1 | 5/2002 | Miedzius et al. |
| 6,467,498 B1 | 10/2002 | Esmailzadeh |
| 6,491,062 B1 | 12/2002 | Croft |
| 6,520,431 B2 | 2/2003 | Donovan |
| 6,524,681 B1 | 2/2003 | Seitz et al. |
| 6,635,172 B2 | 10/2003 | Newman |
| 6,684,900 B1 | 2/2004 | McKeague |
| 6,711,758 B1 | 3/2004 | Terek et al. |
| 6,820,635 B1 | 11/2004 | McKeague |
| 6,880,566 B2 | 4/2005 | Newman |
| 6,948,512 B2 | 9/2005 | McKeague |
| 7,093,608 B2 | 8/2006 | Taylor |
| 7,178,739 B2 | 2/2007 | Taylor |
| 7,240,852 B2 | 7/2007 | Taylor |
| 7,240,853 B2 | 7/2007 | Taylor |
| 7,240,854 B2 | 7/2007 | Taylor |
| 7,276,159 B2 | 10/2007 | Taylor et al. |
| 7,434,781 B2 | 10/2008 | Taylor et al. |
| 7,497,228 B2 | 3/2009 | Taylor et al. |
| 8,321,806 B2 | 11/2012 | Agrusa et al. |
| 9,151,023 B2 | 10/2015 | Taylor et al. |
| 2002/0029412 A1 | 3/2002 | Veal |
| 2002/0043490 A1 | 4/2002 | Newman |
| 2002/0053104 A1 | 5/2002 | Rump et al. |
| 2002/0069457 A1 | 6/2002 | Meier et al. |
| 2002/0073482 A1 | 6/2002 | Hashemi |
| 2002/0092090 A1 | 7/2002 | Johnson |
| 2002/0117214 A1 | 8/2002 | Tucker et al. |
| 2002/0144952 A1 | 10/2002 | Saxton |
| 2002/0157176 A1 | 10/2002 | Wawrla et al. |

(56) References Cited

U.S. PATENT DOCUMENTS

| | | |
|---|---|---|
| 2002/0157708 A1 | 10/2002 | Goff |
| 2002/0162166 A1 | 11/2002 | Saar et al. |
| 2002/0194670 A1 | 12/2002 | Hashemi |
| 2003/0041370 A1 | 3/2003 | Chung |
| 2003/0057155 A1 | 3/2003 | Husain et al. |
| 2003/0066125 A1 | 4/2003 | Guler |
| 2003/0102450 A1 | 6/2003 | Parsons et al. |
| 2003/0155443 A1 | 8/2003 | Ace-Kirker |
| 2003/0193036 A1 | 10/2003 | Mike |
| 2004/0031446 A1 | 2/2004 | Harrison |
| 2004/0054484 A1 | 3/2004 | Farabaugh et al. |
| 2004/0054851 A1 | 3/2004 | Acton et al. |
| 2004/0068784 A1 | 4/2004 | Muderlak |
| 2004/0079689 A1 | 4/2004 | Taylor et al. |
| 2004/0143893 A1 | 7/2004 | Wu et al. |
| 2004/0197922 A1 | 10/2004 | Cooper |
| 2004/0238028 A1 | 12/2004 | Taylor |
| 2004/0238037 A1 | 12/2004 | Taylor et al. |
| 2004/0238458 A1 | 12/2004 | Taylor et al. |
| 2004/0252556 A1 | 12/2004 | Taylor et al. |
| 2005/0273924 A1 | 12/2005 | Taylor |
| 2005/0273925 A1 | 12/2005 | Taylor |
| 2005/0274812 A1 | 12/2005 | Taylor |
| 2005/0279846 A1 | 12/2005 | Taylor |
| 2008/0017589 A1 | 1/2008 | Taylor |
| 2010/0263295 A1 | 10/2010 | Flanagan |

FOREIGN PATENT DOCUMENTS

| | | |
|---|---|---|
| CA | 2334961 | 8/2007 |
| CA | 2570161 | 7/2013 |
| CA | 2430686 | 10/2013 |
| CA | 2822237 | 3/2016 |
| FR | 2715986 | 8/1995 |
| FR | 2754554 | 4/1998 |
| GB | 2452311 | 3/2009 |
| WO | 9964975 | 12/1999 |
| WO | 2005124494 | 12/2005 |
| WO | 2011047246 | 4/2011 |

OTHER PUBLICATIONS

Taylor; U.S. Patent Application entitled: Systems and Methods for Controlling Flushing Apparatus and Related Interfaces having U.S. Appl. No. 13/117,963, filed May 27, 2011, 41 pgs.

Newman, Michael; International Search Report for serial No. PCT/US1999/013296, filed Jun. 11, 1999, dated Aug. 30, 1999, 3 pgs.

Taylor, Thomas; Office Action from Canadian Intellectual Property Office for Application No. 2,430,686, filed May 30, 2003, dated Jun. 20, 2012, 3 pgs.

Goslin, David; Canadian Office Action for serial No. 2,822,237, filed Aug. 13, 2013, dated Jan. 6, 2015, 4 pgs.

Taylor, Thomas; International Preliminary Report on Patentability for serial No. PCT/US2005/019941, filed Jun. 8, 2005, dated Dec. 14, 2006, 5 pgs.

Taylor, Thomas; International Search Report for serial No. PCT/US2005/019941, filed Jun. 8, 2005, dated Dec. 5, 2005, 3 pgs.

Taylor; Office Action from Canadian Intellectual Property Office for Application No. 2,570,161, filed Dec. 8, 2006, dated May 3, 2012; 2 pgs.

Australian Patent Examination Report for application No. 2011202554, filed Jun. 1, 2011, dated Sep. 25, 2014, 3 pgs.

Taylor, Thomas; Mexico Office Action for serial No. MX/a/2012/005832, filed May 18, 2012, dated Jul. 17, 2014, 7 pgs.

Taylor; European Search Report for serial No. 12/,169,186.9, filed May 24, 2012, dated Aug. 8, 2012, 7 pgs.

Taylor, Thomas M.; European Office Action for serial No. 12169186.9, filed May 24, 2012, dated May 12, 2015, 4 pgs.

Taylor, Thomas; U.S. Provisional Patent Application entitled: Water Flushing System, having U.S. Appl. No. 60/474,467, filed May 31, 2003, 73 pgs.

Newman, Michael; Notice of Allowance for U.S. Appl. No. 10/691,289, filed Oct. 20, 2003, dated Oct. 27, 2004, 14 pgs.

Newman, Michael; Non-Final Office Action for U.S. Appl. No. 10/691,289, filed Oct. 20, 2003, dated Mar. 11, 2004, 7 pgs.

Newman, Michael; U.S. Patent Application entitled: Apparatus for the Enhancement of Water Quality in a Subterranean Pressurized Water Distribution System, having U.S. Appl. No. 10/691,289, filed Oct. 20, 2003, 30 pgs.

Taylor, Thomas; Examiner Interview Summary Record for U.S. Appl. No. 10/856,000, filed May 28, 2004, dated Apr. 26, 2007, 5 pgs.

Taylor, Thomas; Final Office Action for U.S. Appl. No. 10/856,000, filed May 28, 2004, dated Dec. 21, 2006, 6 pgs.

Taylor, Thomas; Issue Notification for U.S. Appl. No. 10/856,000, filed May 28, 2004, dated Sep. 12, 2007, 1 pg.

Taylor, Thomas; Non-final Office Action for U.S. Appl. No. 10/856,000, filed May 28, 2004, dated May 8, 2006, 9 pgs.

Taylor, Thomas; Notice of Allowance for U.S. Appl. No. 10/856,000, filed May 28, 2004, dated May 30, 2007, 4 pgs.

Taylor, Thomas; Restriction Requirement for U.S. Appl. No. 10/856,000, filed May 28, 2004, dated Feb. 1, 2006, 5 pgs.

Taylor; Thomas; U.S. Patent Application entitled: Water Flushing System, having U.S. Appl. No. 10/856,000, filed May 28, 2004, 78 pgs.

Taylor, Thomas; Non-Final Office Action for U.S. Appl. No. 11/865,631, filed Oct. 1, 2007, dated Jul. 18, 2008, 20 pgs.

Taylor, Thomas; Restriction Requirement for U.S. Appl. No. 11/865,631, filed Oct. 1, 2007, dated Mar. 18, 2008, 7 pgs.

Taylor, Thomas; U.S. Patent Application entitled: Water Flushing System Providing Treated Discharge, having U.S. Appl. No. 11/865,631, filed Oct. 1, 2007, 71 pgs.

Taylor, Thomas Moriz; Notice of Allowance for U.S. Appl. No. 13/117,963, filed May 27, 2011, dated Jun. 3, 2015, 9 pgs.

Taylor, Thomas; Issue Notification for U.S. Appl. No. 10/856,003, filed May 28, 2004, dated Feb. 11, 2009, 1 pg.

Taylor, Thomas; Non-Final Office Action for U.S. Appl. No. 10/856,003, filed May 28, 2004, dated Jan. 11, 2007, 10 pgs.

Taylor, Thomas; Non-Final Office Action for U.S. Appl. No. 10/856,003, filed May 28, 2004, dated Jul. 26, 2007, 7 pgs.

Taylor, Thomas; Notice of Allowance for U.S. Appl. No. 10/856,003, filed May 28, 2004, dated Nov. 10, 2008, 6 pgs.

Taylor, Thomas; U.S. Patent Application entitled: Freeze and Backflow Protection for a Subterranean Water Flushing System, having U.S. Appl. No. 10/856,003, filed May 28, 2004, 76 pgs.

Taylor, Thomas;Final Office Action for U.S. Appl. No. 10/856,003, filed May 28, 2004, dated Apr. 17, 2008, 8 pgs.

Taylor, Thomas; Final Office Action for U.S. Appl. No. 10/856,035, filed May 28, 2004, dated Oct. 30, 2007, 8 pgs.

Taylor, Thomas; Issue Notification for U.S. Appl. No. 10/856,035, filed May 28, 2004, dated Sep. 24, 2008, 1 pg.

Taylor, Thomas; Non-Final Office Action for U.S. Appl. No. 10/856,035, filed May 28, 2004, dated May 16, 2006, 13 pgs.

Taylor, Thomas; Non-Final Office Action for U.S. Appl. No. 10/856,035, filed May 28, 2004, dated Jan. 3, 2007, 7 pgs.

Taylor, Thomas; Notice of Allowance for U.S. Appl. No. 10/856,035, filed May 28, 2004, dated Jun. 12, 2008, 16 pgs.

Taylor, Thomas; U.S. Patent Application entitled: Remotely Actuated Quick Connect/Disconnect Coupling, having U.S. Appl. No. 10/856,035, filed May 28, 2004, 77 pgs.

Taylor, Thomas; Notice of Allowance for U.S. Appl. No. 10/856,465, filed May 28, 2004, dated Mar. 10, 2006, 12 pgs.

Taylor, Thomas; U.S. Patent Application entitled: Vacuum Pressure Breaker and Freeze Protection for a Water Flushing System, having U.S. Appl. No. 10/56,465, filed May 28, 2004, 76 pgs.

Taylor, Thomas; Issue Notificaiton for U.S. Appl. No. 10/864,560, filed Jun. 9, 2004, dated Jan. 31, 2007, 1 pg.

Taylor, Thomas; Non-Final Office Action for U.S. Appl. No. 10/864,560, filed Jun. 9, 2004, dated Mar. 13, 2006, 14 pgs.

Taylor, Thomas; Notice of Allowance for U.S. Appl. No. 10/864,560, filed Jun. 9, 2004, dated Oct. 11, 2006, 6 pgs.

Taylor, Thomas; U.S. Patent Application entitled: Automatic Stagnant Water Flushing System, having U.S. Appl. No. 10/864,560, filed Jun. 9, 2004, 42 pgs.

(56) References Cited

OTHER PUBLICATIONS

Taylor, Thomas; Issue Notification for U.S. Appl. No. 10/864,718, filed Jun. 9, 2004, dated Jun. 20, 2007, 1 pg.
Taylor, Thomas; Non-Final Office Action for U.S. Appl. No. 10/864,718, filed Jun. 9, 2004, dated Mar. 13, 2006, 12 pgs.
Taylor, Thomas; Notice of Allowance for U.S. Appl. No. 10/864,718, filed Jun. 9, 2004, dated Mar. 14, 2007, 6 pgs.
Taylor, Thomas; U.S. Patent Application entitled: Drinking Fountain with Automatic Stagnant Water Flushing System, having U.S. Appl. No. 10/864,718, filed Jun. 9, 2004, 38 pgs.
Taylor, Thomas; Issue Notification for U.S. Appl. No. 10/864,725, filed Jun. 9, 2004, dated Jun. 20, 2007, 1 pg.
Taylor, Thomas; Non-Final Office Action for U.S. Appl. No. 10/864,725, filed Jun. 9, 2004, dated Mar. 14, 2006, 12 pgs.
Taylor, Thomas; Notice of Allowance for U.S. Appl. No. 10/864,725, filed Jun. 9, 2004, dated Mar. 14, 2007, 6 pgs.
Taylor, Thomas; U.S. Patent Application entitled: Emergency Shower with Automatic Stagnant Water Flushing System, having U.S. Appl. No. 10/864,725, filed Jun. 9, 2004, 38 pgs.
Taylor, Thomas; Issue Notification for U.S. Appl. No. 10/864,743, filed Jun. 9, 2004, dated Jun. 20, 2007, 1 pgs.
Taylor, Thomas; Non-Final Office Action for U.S. Appl. No. 10/864,743, filed Jun. 9, 2004, dated Mar. 14, 2006, 12 pgs.
Taylor, Thomas; Notice of Allowance for U.S. Appl. No. 10/864,743, filed Jun. 9, 2004, dated Mar. 14, 2007, 6 pgs.
Taylor, Thomas; U.S. Patent Application entitled: Eyewash with Automatic Stagnant Water Flushing System, having U.S. Appl. No. 10/864,743, filed Jun. 9, 2004, 37 pgs.
Taylor, Thomas Moriz; Final Office Action for U.S. Appl. No. 13/117,963, filed May 27, 2011, dated Apr. 3, 2014, 16 pgs.
Taylor, Thomas Moriz; Final Office Action for U.S. Appl. No. 13/117,963, filed May 27, 2011, dated Aug. 1, 2013; 22 pgs.
Taylor, Thomas Moriz; Issue Notification for U.S. Appl. No. 13/117,963, filed May 27, 2011, dated Sep. 16, 2015, 1 pg.
Taylor, Thomas Moriz; Non-Final Office Action for U.S. Appl. No. 13/117,963 filed May 27, 2011, dated Dec. 17, 2013; 23 pgs.
Taylor, Thomas Moriz; Non-Final Office Action for U.S. Appl. No. 13/117,963, filed May 27, 2011, dated Feb. 27, 2013; 43 pgs.
Taylor, Thomas; Office Action for Canadian patent application No. 2,741,889, filed May 31, 2011, dated Jun. 5, 2017, 3 pgs.
Taylor, Thomas; Office Action for European application No. 12169186.9, filed May 24, 2012, dated Dec. 11, 2017, 5 pgs.

\* cited by examiner

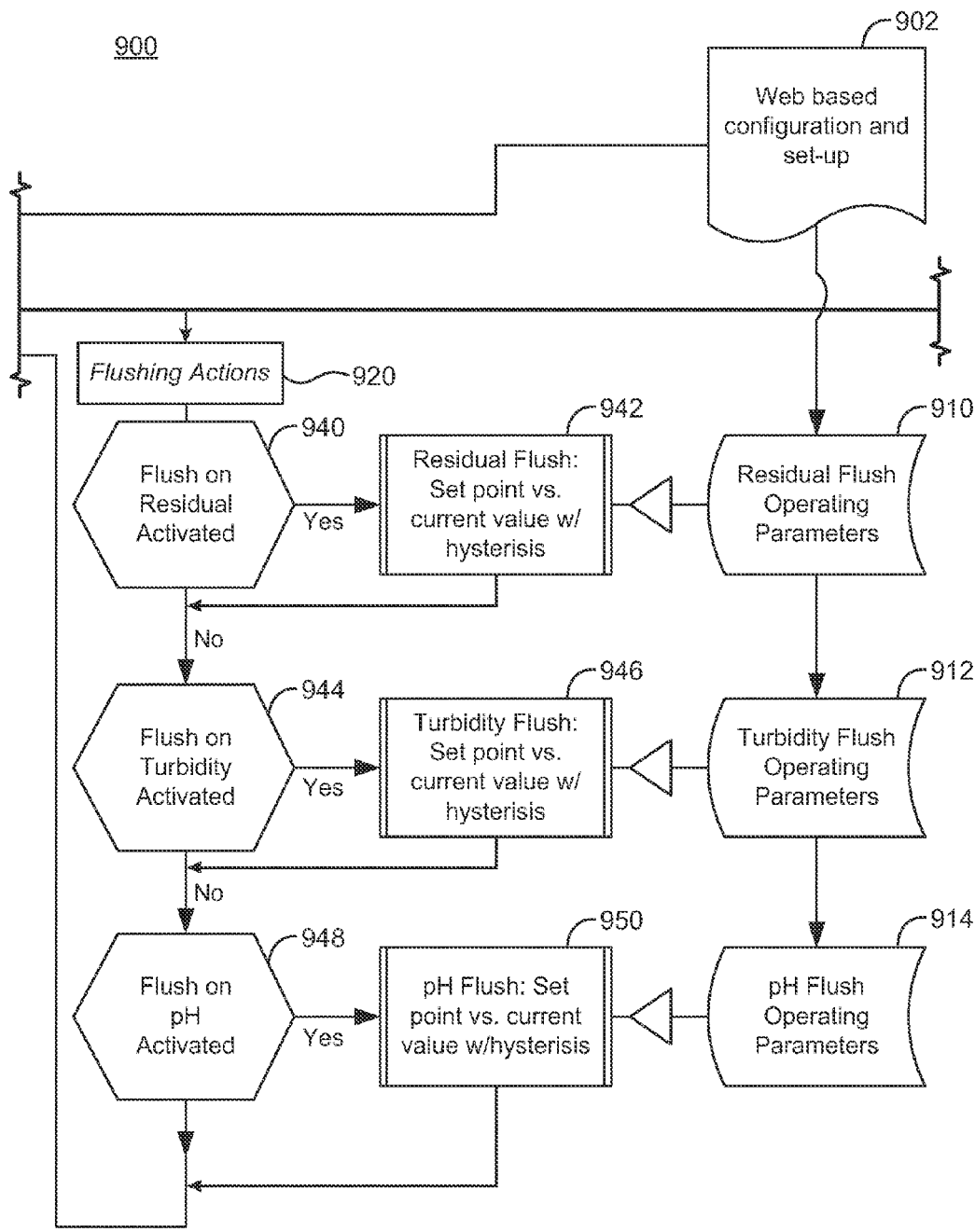
FIG. 9 (cont.1)

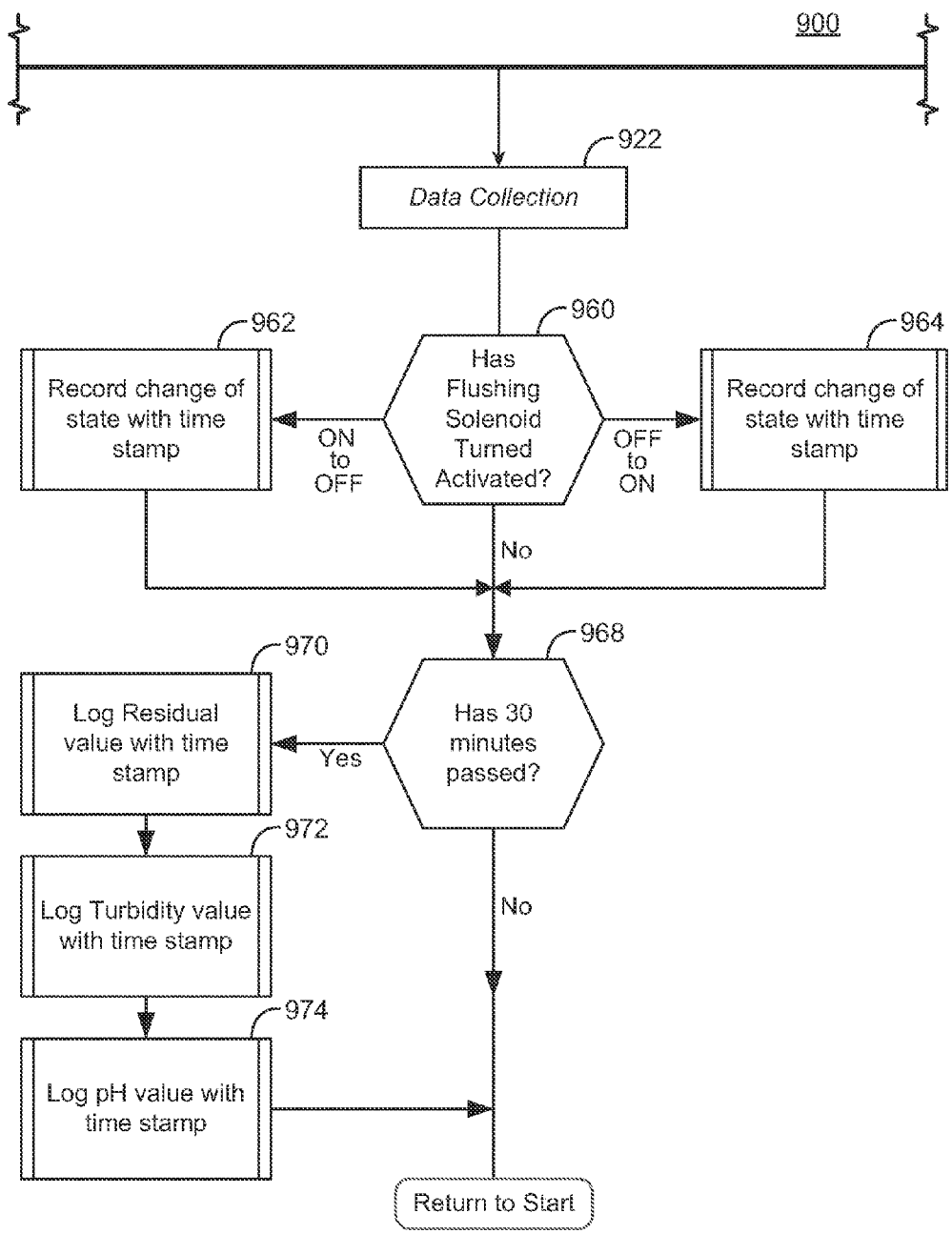
FIG. 9 (cont.2)

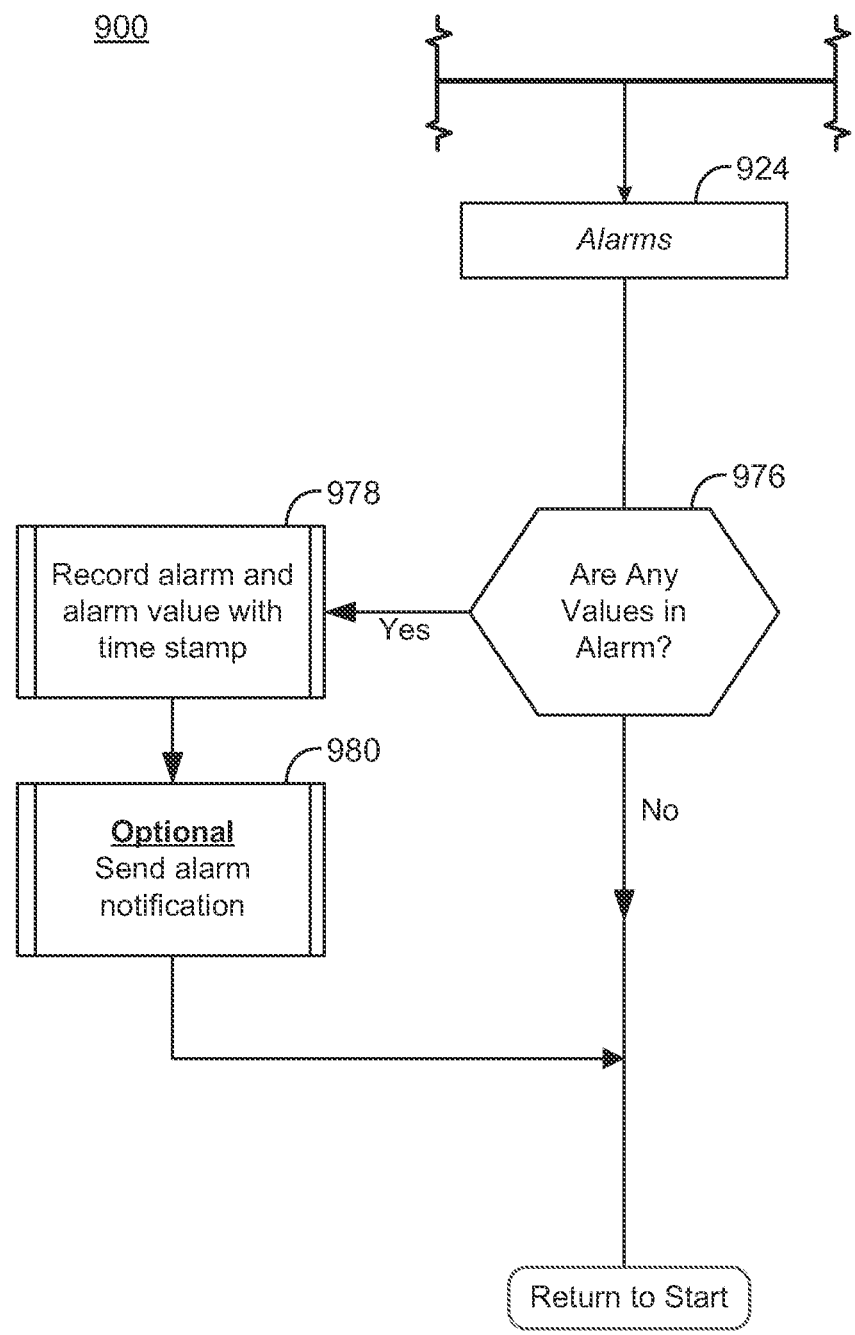
FIG. 9 (cont.3)

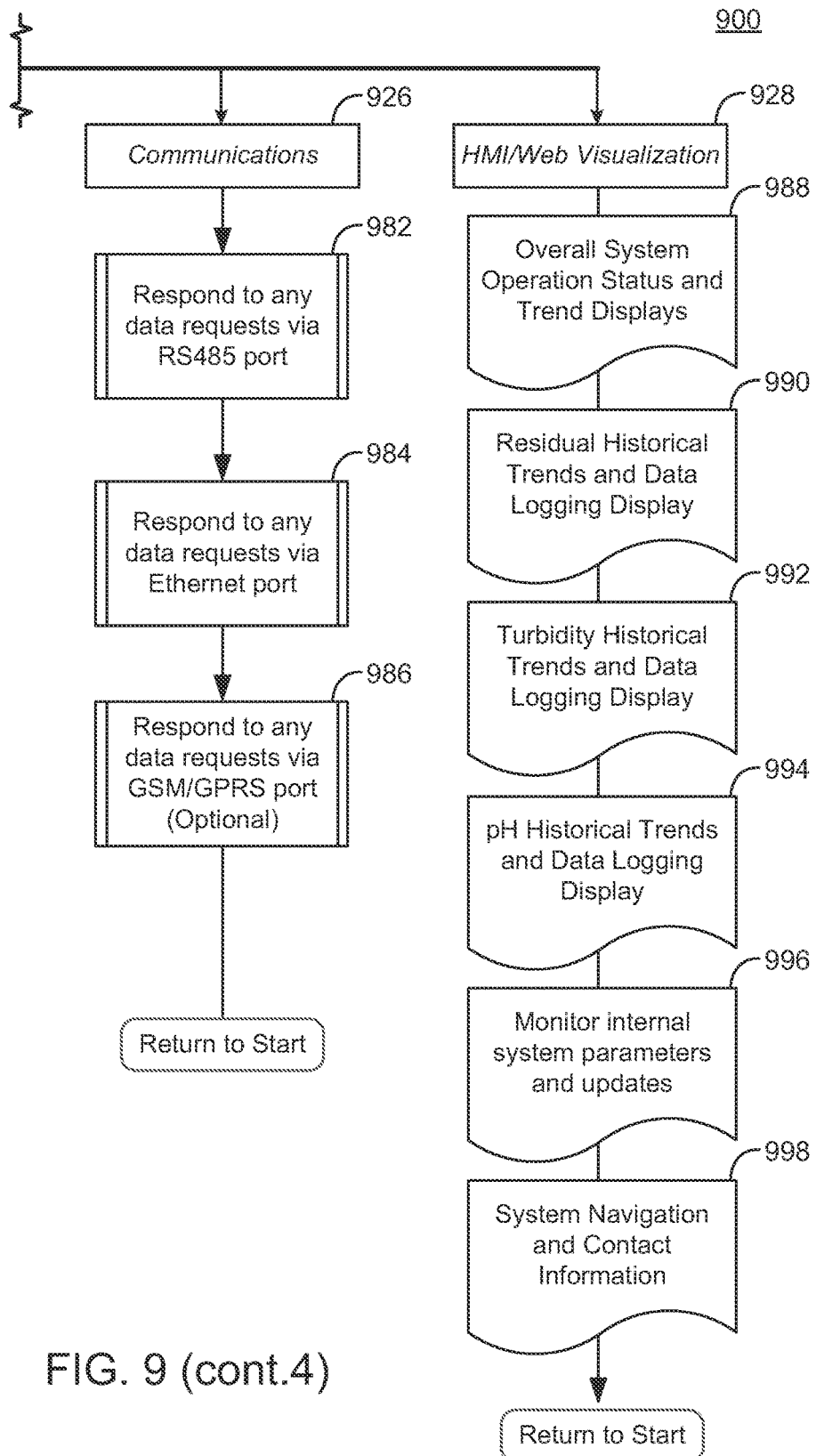
FIG. 9 (cont.4)

SYSTEMS AND METHODS FOR CONTROLLING FLUSHING APPARATUS AND RELATED INTERFACES

CROSS-REFERENCE TO RELATED APPLICATIONS

This application is a continuation of U.S. patent application Ser. No. 13/117,963, filed May 27, 2011, the entire disclosure of which is hereby incorporated by reference.

FIELD

The present disclosure relates in general to programmable water quality maintenance devices and more particularly to a programmable water sampling and purging apparatus for monitoring and maintaining water quality in a subterranean or partially subterranean water distribution system. The present disclosure further relates to interfaces for controlling a water sampling-flushing apparatus.

BACKGROUND

Underground water distribution systems for residential and commercial areas often incorporate low flow or dead end portions by design. For instance, fire protection and land development codes often require oversized water mains for anticipated fire control and peak water demands. Such design features, although in the best interest of the community, have the effect of dramatically reducing water flow velocity and potentially increasing instances of poor water quality areas within a water distribution system. The problem is further exacerbated by water distribution systems that experience large seasonal fluctuations in demand. These systems often experience additional reduction in water flow during non-seasonal periods of the year.

Low water flow conditions and corresponding increases in water retention time within portions of the water distribution system have the potential to degrade the chemical and microbiological quality of water transported through the distribution system. Degradation in water quality can result from prolonged exposure to water system materials, internal sedimentation, and/or contaminant deposits within a piping system. Disinfectants are commonly used in an effort to control bacterial growth. However, as disinfectant residuals dissipate, bacterial regrowth occurs.

In the United States, the Environmental Protection Agency (EPA) sets standards for tap water and public water systems under the Safe Drinking Water Act (SDWA). The SDWA requires that potable, or drinkable, water systems maintain minimum disinfectant residual levels, to prevent the regrowth of bacteria. Mandatory testing programs exist to track compliance and identify potential health hazards. Water systems failing to adhere to regulatory or operational water quality standards are subject to regulatory enforcement action, public disclosure of health hazards, and increased public and regulatory scrutiny.

Additionally, corrosion rates in low flow and stagnant areas can escalate as chemical reactions and microbiological activity increase. Corrosive water tends to dissolve certain materials commonly used in the construction of water distribution systems. The two primary metals of concern are iron and lead. Iron is commonly found in piping system materials. Lead is commonly found in older water systems that have incorporated lead joints, lead composite pipes and/or brass fittings. Elevated iron concentrations can result in violations of drinking water standards. In both potable and non-potable water distribution systems, excessive concentrations of iron can result in staining of structure surfaces, fixtures and clothing.

Water distribution system compliance with water quality regulatory standards can be evaluated through the collection and analysis of water samples. Samples can be collected from plumbing systems and stationary water sampling stations installed within a water system distribution system. These designated sampling locations often produce test results that are either inaccurate or not representative of water quality throughout the water distribution system. Furthermore, collected data is only useful if it can be evaluated promptly. When human resources are required for such evaluations, this can lead to increased cost.

One approach to addressing water quality degradation in low flow or dead end areas has been to dispatch workers, on an incidental basis, to manually purge the water from a problem area of a system. This method is contingent on financial and human resource availability.

An approach to supplement manual flushing operations is the monitoring of increased concentrations of disinfectant residuals, in an attempt to counteract the effects of disinfectant residual dissipation, which is a time dependent function of chemical and biological reactions. Using this approach, the disinfectant residual level of the entire system is increased or, alternatively, disinfectant booster stations are positioned at strategic areas along the water distribution system. Disinfectants break down over time and thereby become less effective. Therefore, disinfectant levels must be maintained at appropriate levels. For example, the Federal Safe Drinking Water Act is expected to establish a maximum limit of 4 mg/l for chlorine.

The complexity of water quality as a subject is reflected in the many types of measurements of water quality indicators. Some of the following measurements are possible in direct contact with a water source in question: temperature, pH, dissolved oxygen, conductivity, Oxygen Reduction potential (ORP), turbidity, Secchi disk depth, requiring direct contact with the water source in question. More complex measurements can sometimes require a lab setting for which a water sample must be collected, preserved, and analyzed at another location. Making these complex measurements can be expensive. Because direct measurements of water quality can be expensive, monitoring programs are typically conducted by government agencies. The cost of implementation of monitoring programs can be reduced by automating sampling and flushing operations. In at least one implementation of the technology, water conditions can be tested or monitored by a programmable apparatus. A programmable apparatus can be configured to receive monitoring and maintenance instructions. Instructions can be input through one or more interfaces via an electronic device in signal communication with a programmable apparatus.

There exist apparatuses capable of analyzing water quality and purging low quality water from low flow or dead end areas of water distribution systems. See for example, U.S. Pat. No. 6,035,704 and U.S. Pat. No. 6,880,556 to Newman, which are fully incorporated by reference herein. These apparatuses provide for the analytical and purging function of the apparatus to be controllable by a remotely operated device. However, the existing apparatuses can be improved upon through better monitoring: methods and increased levels of automation within this technology.

DETAILED DESCRIPTION

Figure 1:
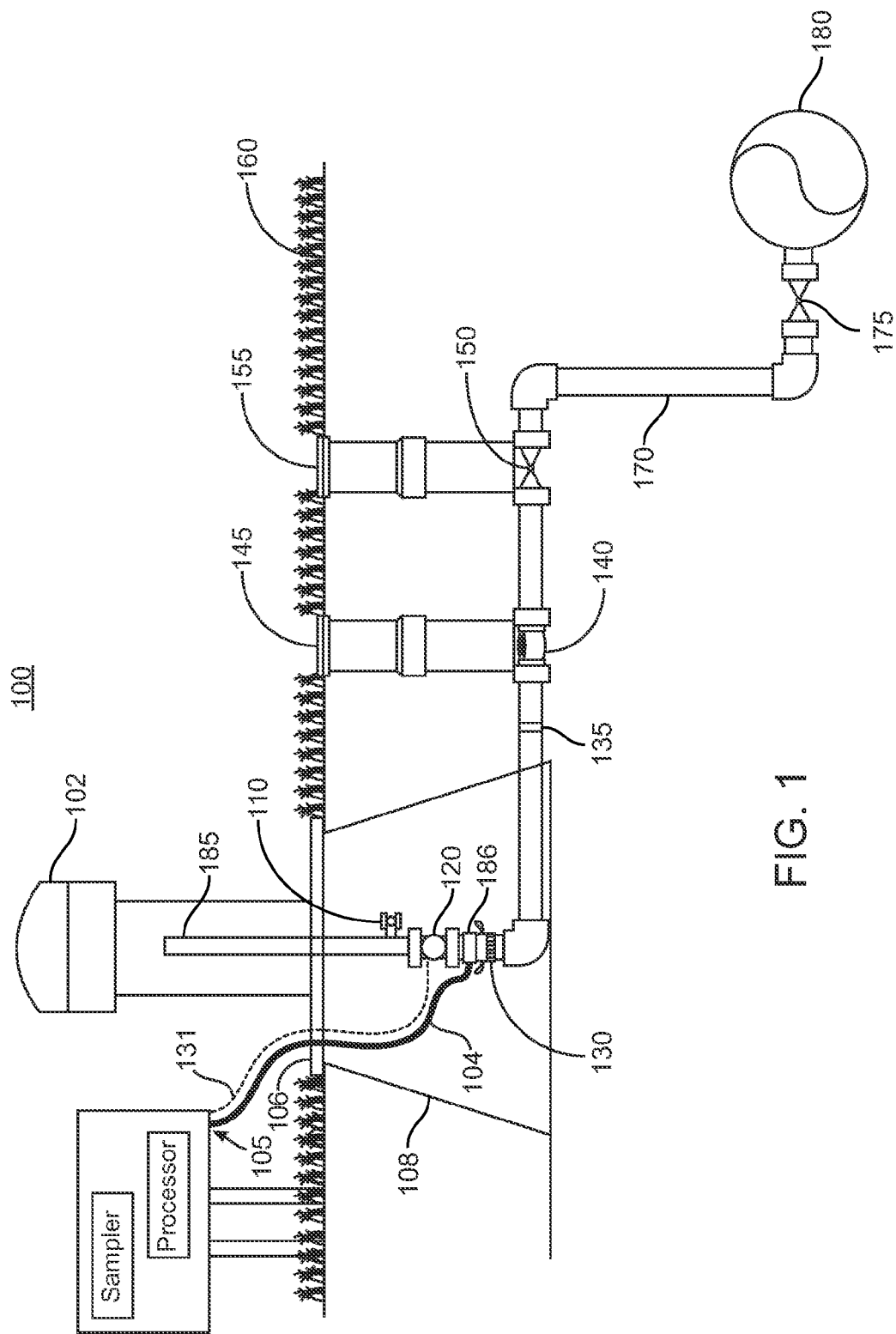
FIG. 1 illustrates a water flushing station within the technology

As will be appreciated for simplicity and clarity of illustration, where appropriate, reference numerals have been repeated among the different figures to indicate corresponding or analogous elements. In addition, numerous specific details are set forth in order to provide a thorough understanding of the implementations described herein. However, it will be understood that the implementations described herein can be practiced without these specific details. In other instances, methods, procedures and components have not been described in detail so as not to obscure the related relevant feature being described. Also, the description is not to be considered as limiting the scope of the implementations of the technology described herein.

The technology includes methods, uses and implementations of one or more programs executable by a processor. The technology includes methods, uses and implementations pertaining to controls, including digital controls for dynamic systems. See *Modern Control Systems*, by Richard Dorf and *Digital Control of Dynamic Systems*, by Gene Franklin for discussions of control theory. *Modern Control Systems* and *Digital Control of Dynamic Systems* are fully incorporated by reference herein.

Several definitions that apply throughout the disclosure of the technology will now be presented. The word "coupled" is defined as connected, whether directly or indirectly through intervening components, and is not necessarily limited to physical connections. The term "communicatively coupled" is defined as connected, whether directly or indirectly through intervening components, is not necessarily limited to a physical connection, and allows for the transfer of data. The term "electronic device" is defined as any electronic device that is capable of at least accepting information entries from a user and includes the device's own power source. A "wireless communication" includes communication that occurs without wires using electromagnetic radiation. The term "memory" refers to transitory memory and non-transitory memory. For example, non-transitory memory can be implemented as Random Access Memory (RAM), Read-Only Memory (ROM), flash, ferromagnetic, phase-change memory, and other non-transitory memory technologies. "Coupled" refers to a relationship between items which may have one or more intermediate parts or items to which they are connected. "Reagent" refers to a substance or compound that is added to a system in order to bring about a chemical reaction or is added to determine if a reaction occurs. "pH" is a measure of the acidity or basicity of an aqueous solution. (Pure water is considered to be neutral, with a pH close to 7.0 at 25° C. (77° F.)). Solutions with a pH less than 7 are said to be acidic and solutions with a pH greater than 7 are basic or alkaline. "Drinking water" or "potable water" is water of sufficiently high quality that it can be consumed or used with low risk of immediate or long term harm to humans or large animals. "Sampling" is the reduction of a continuous signal to a discrete signal. A common example is the conversion of a sound wave (a continuous signal) to a sequence of samples (a discrete-time signal). A "sample" refers to a value or set of values at a point in time and/or space. A "water sample" can include sampled water or data associated with sampled water. "Sampling frequency" or "sampling rate" is the number of samples obtained in a given period of time. "Turbitity" is the cloudiness or haziness of a fluid caused by individual particles (suspended solids) that are generally invisible to the naked eye. Turbidity can be used as an indicator of water quality. "Disinfectant residual" or simply "residual" is a measure of the amount of disinfectant present in a given volume of water, and can be expressed in the units such as mg/L (miligrams per Liter). "Firmware" includes fixed, often relatively small, programs and/or data structures that internally control various electronic devices. "Programmable logic device" or PLD is an electronic component used to build reconfigurable digital circuits. A PLD has an undefined function at the time of manufacture and before a PLD can be used in a circuit it must be programmed. "Operator" can refer to a human being or an electronic device configured to receive signals and send instructions. "Window" includes at least a display of a device and a web page.

The needs of individual water distributions systems and the needs of water sources within systems can vary according to many parameters, including the intended use of the water, the environmental conditions in which water resides and the demand for water in a given area or region. As will be discussed below, it can be beneficial to flush or clear water in a certain area. Thus, it can be important to monitor and control flushing operations under changing conditions.

Reference will now be made in detail to implementations of the technology. Each example is provided by way of explanation of the technology only, not as a limitation of the technology. It will be apparent to those skilled in the art that various modifications and variations can be made in the present technology. For instance, features described as part of one implementation of the technology can be used on another implementation to yield a still further implementation. Thus, it is intended that the present technology cover such modifications and variations that come within the scope of the technology.

FIG. 1 illustrates an example implementation of a water monitoring and flushing station 100 within the technology. Programming interface 102 enables data to be received by and sent from a processor. Sample port 105, connects a sampler to a water source via a sample line 104, and enables water samples to be collected for analysis from a sampling point 186. Communication between the solenoid controlled valve 120 can be enabled via a wire 131. In some implementations, communication can be wireless. Splash guard 106 which is connected to base 108, shields components within the base from flushed water and minimizes erosion. Splash guard 106 may be constructed of plastic or other suitable materials. The base 108, which may be at least partially subterranean, maintains the system in an upright configuration, as shown. Within the base 108, a low pressure relief valve 110 may be provided in order to enable the manual draining of the system. Proximate the relief valve is control valve 120 for activation during flushing operations.

The control valve can be interposed along a flow line between the relief valve 110 and a cam-lock release system 130. The cam-lock release system 130 can be provided to enable the components of the system 100 which are above it to be removed. The system 100 can be connected to the remainder of the line 185 at a male thread point 135. The line can connected to a flow meter 140 within a flow meter housing 145 and a curb stop 150 within a curb stop housing 155. The line is further comprised by a pipe 170 which is coupled to the system 100. The pipe 170 can be connected to a distribution line 180 via a corp stop 175. As illustrated in FIG. 1, some of the components of the system reside above ground level 160, and some components reside below ground level 160. It will be understood that other configurations are possible within the technology and that in some configurations all components described above may not be present. Furthermore, additional components may be added within the technology.

In at least one implementation of the technology, one or more probes are used to evaluate water properties. Probes can be used to measure chlorine or chloramine levels, or the levels of other disinfectants. Probes can be used to measure or test for temperature, pH and turbidity or temperature, pH or turbidity, or any combination thereof. Probes are an example of a water sampling device.

Figure 2:
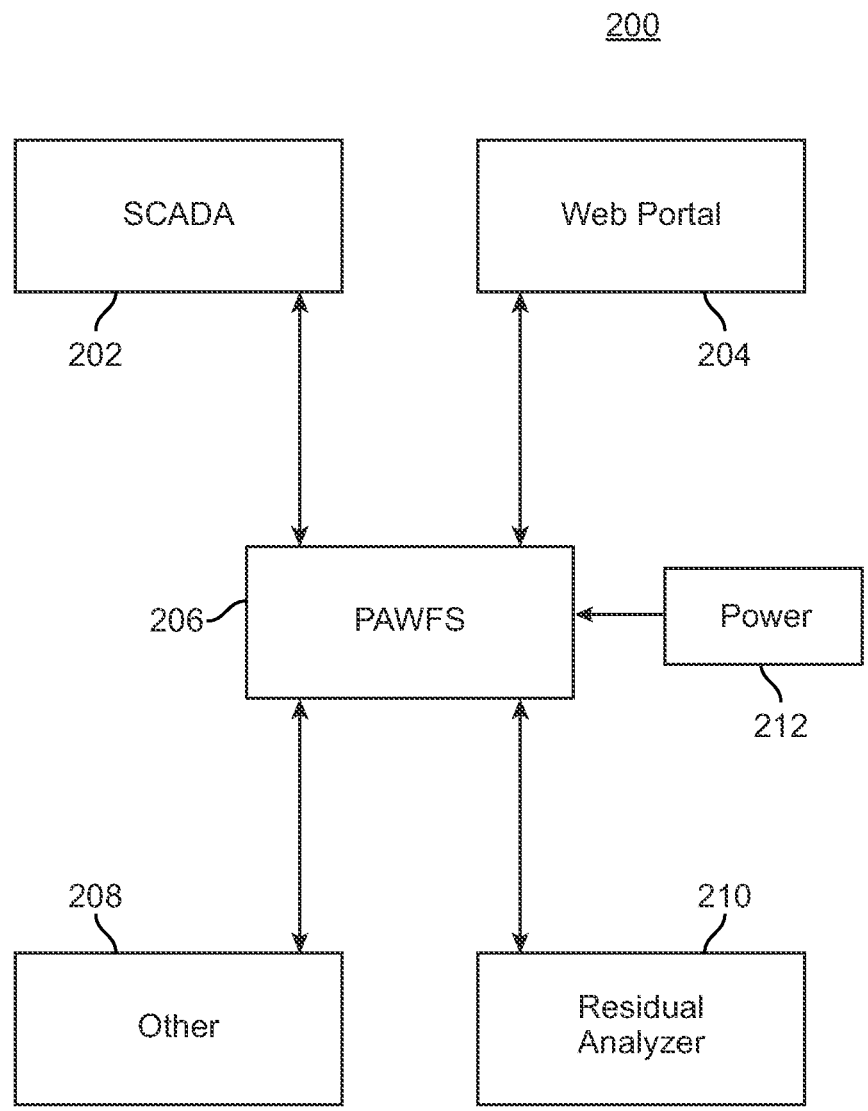
FIG. 2 illustrates a block diagram of a water flushing control network within the technology.

Referring to FIG. 2, an example programmable automatic water flushing system (PAWFS) 206 powered by a power source 212 can be communicatively coupled to a remote apparatus such as a supervisory control and data acquisition system 202 (also known as a SCADA), or to a web portal 204 or a web page. A PAWFS can be connected or coupled to a residual analyzer 210 or other devices 208 such as probes or meters, and the like. Again, it will be noted that FIG. 2 and the other figures illustrate non-limiting examples, and modifications may be necessary to make a system work in particular network environments.

As shown in FIG. 2, in at least one implementation of the technology, the PAWFS can be powered by a single phase 120V (60 Hz) or a single phase 220V (60 Hz) source 212. The power source 212 can be internal or external to the system 100.

Figure 3:
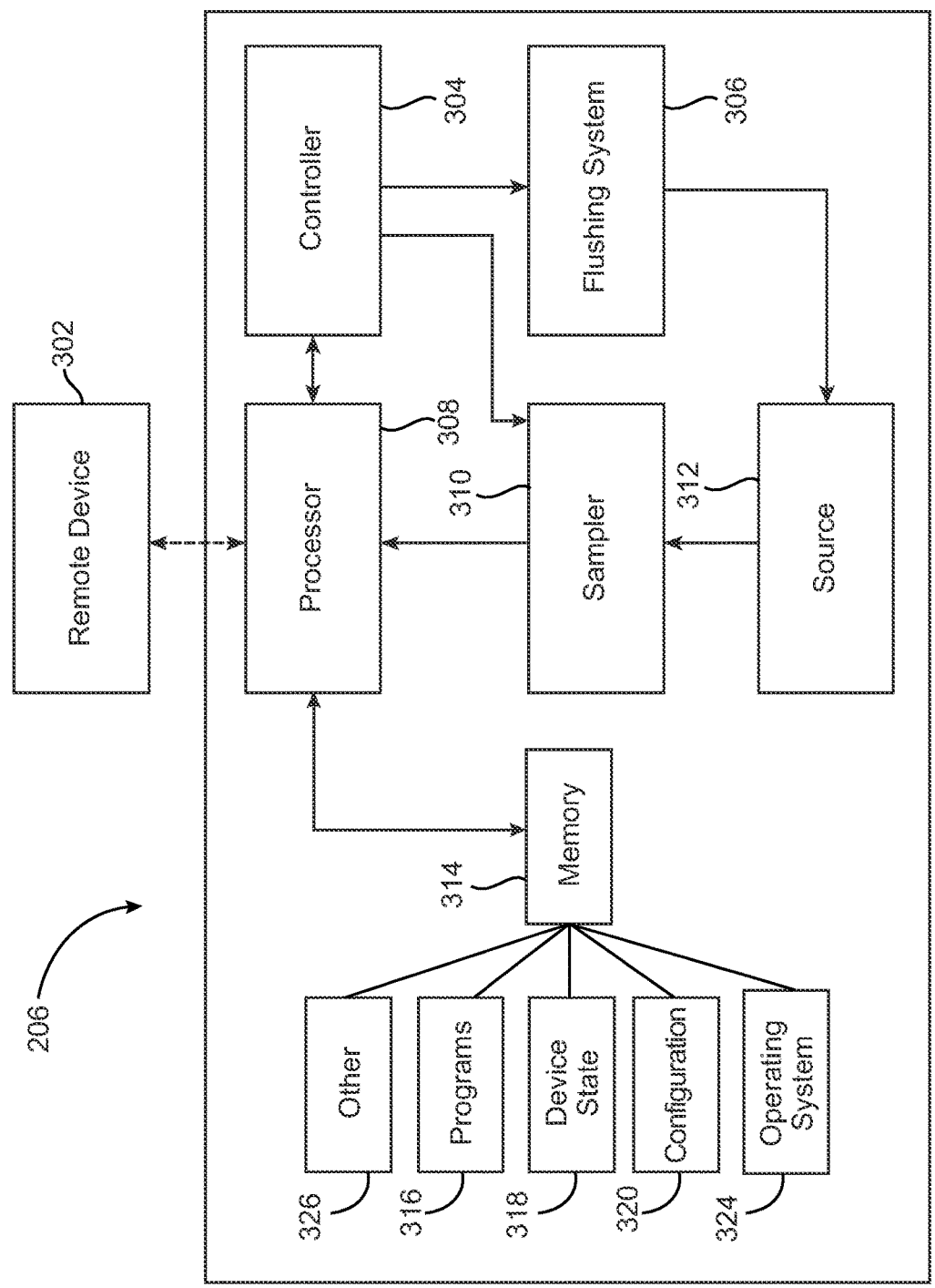
FIG. 3 illustrates a block diagram of a programmable automatic water flushing system (PAWFS) communicatively coupled to a remote electronic device within the technology.

With reference to FIG. 3, a block diagram of a PAWFS device 206 in accordance with an example implementation is illustrated. As shown, the device 206 can include a processor 308 that controls the operation of the PAWFS 206, such as facilitating communications with a remote device 302 at remote locations, sending signals to a controller 304, receiving signals from a controller 304, receiving data from a sampling device 310, executing programs 316 stored in memory 314, providing a graphical user interface, and so forth. A communication subsystem (not shown) performs communication transmission and reception with a remote device 302. Additionally, in at least one implementation, the processor 308 can be coupled to a serial port (for example, a Universal Serial Bus port, not shown) that facilitates communication with other devices or systems via the serial port. A display can be communicatively coupled to the processor 308 to facilitate display of information to an operator of the flushing system 306. The remote device 302 can be equipped with a keyboard, which can be physical or virtual (for example, displayed), and the keyboard can be communicatively coupled to the processor 308. Other subsystems 326 and other device subsystems (e.g., 208) are generally indicated as communicatively coupled with the processor 308. An example of a communication subsystem is a short-range communication system such as a BLUETOOTH® communication module or a WI-FI® communication module (a communication module in compliance with IEEE 802.11b) and associated circuits and components. Long range communication to a remote device can be via 400-900 MHz radio signals, micro-wave radio signals or by Ethernet based radio signals. Additionally, the processor 308 can perform operating system functions and executes programs 316 or software applications within the PAWFS 206. Programs 316 can be executed according to software or firmware stored in memory 314. Water collected from a source 312 (e.g., 186) near a station can be sampled by one or more samplers 310, with the data collected by the sampler input to the processor 308. Water sampling by the sampler can be controlled by the controller 304 in accordance with instructions executed by the processor 308. Sample data can be used by a remote operator 302 to make decisions about flushing operations, or used as a dependent variable for various programs 316 executed by the processor 308. In some implementations, not all of the above components are included in the PAWFS 206. Additionally, an auxiliary I/O subsystem (not shown) can take the form of one or more different navigation tools (multi-directional or single-directional), external display devices such as keyboards, and other subsystems capable of providing input or receiving output from the system 306.

A monitoring apparatus within the system 100 can be configured to send an alarm to a remote location 302 in a predefined set of circumstances, for example, if an action called for by controlling software fails to occur, a fault code or fault signal or both can be generated and relayed as appropriate. An operator at the remote location 302 can then override the system electronics to instruct the system to flush a poor water quality area or take other actions, if desired. Alternatively, an apparatus can be configured to automatically flush the line in this circumstance. Furthermore, an apparatus can be configured to send an alarm and await a signal from a remote location to either flush or not flush a line. If a predetermined amount of time elapses since the alarm signal, the device can send another alarm signal to a remote location or to flush the line.

The processor 308 can be configured to send and receive signals or messages. As will be described in greater detail below, the controller 304 can be enabled to actuate one or more actuators upon the receiving of either remote or local signals. A system within the technology can be equipped with components to enable operation of various programs 316, as shown in FIG. 3. As shown, the memory 314 can provide storage for the operating system 324, device programs 316, data, and the like. The operating system 324 can be generally configured to manage other programs 326 that are also stored in memory and executable on the processor 308. The operating system 324 can handle requests for services made by programs 316 through predefined program interfaces. More specifically, the operating system can typically determine the order in which multiple programs 316 are executed on the processor 308 and the execution time allotted for each program 316, manages the sharing of memory 314 among multiple programs 316, handles input and output to and from other device subsystems, and so forth. In addition, operators can interact directly with the operating system 324 through an interface, either remotely or locally, typically including a keyboard or keypad and a display screen. The operating system 324, programs 316, data, and other information can be stored in memory 314, RAM, read-only memory (ROM), or another suitable storage element (not shown).

A remote electronic device 302 can include a touch-sensitive display or touchscreen that includes one or more touch location sensors, an overlay, and a display, such as a liquid crystal display (LCD) or light emitting diode (LED) display. The touch location sensor(s) can be a capacitive, resistive, infrared, surface acoustic wave (SAW), or other type of touch-sensitive sensor. A touch, or touch contact, can be detected by a touchscreen and processed by the processor of the electronic device or the system processor, for example, to determine a location of the touch. Touch location data can include the center of the area of contact or the entire area of contact for further processing. A touch may be detected from a contact member, such as a body part of a user, for example a finger or thumb, or other objects, for example a stylus, pen, or other pointer, depending on the nature of the touch location sensor. In other examples, the keyboard is a virtual keyboard provided on a touch screen display. Such touch applications can be used to increase the functionality of one or more display screens or windows within the technology, as will be discussed below.

In at least one implementation of the technology, a controller 304 automatically operates an electrical solenoid (e.g., 306) to actuate a water valve (e.g., 120). The controller 304 can be configured to be in signal communication with one or more electronic devices 302 as well as the processor 308. The controller 304 can be of a modular design and be enabled to be retrofitted to an existing flushing apparatus (e.g., 120, 306).

Signal communication with a remote device 302 can be through a cellular network, such as GSM or GPRS networks. The technology can be configured to send and receive serial signal communications via one or more wireless networks. The technology can also be configured to communicate with a remote device 302 via an Ethernet connection, a 400-900 MHz radio, a microwave radio or a BLUETOOTH® device. Other signal connectivities are possible within the technology.

The controller 304 can be programming: using standard programming languages, including Basic and one or more object-oriented languages.

The controller 304 may be configured to comprise the following: 1) digital outputs for control of a flushing solenoid, wherein one output can send an 'open' signal to the solenoid, wherein a second output can send a 'close' signal to the solenoid; 2) a digital input for feedback of operation of the flushing valve position (open or closed); at least one digital input in signal communication with a flow meter; 3) digital input to receive a signal from tamper evident to detect when an enclosure containing the controller has been accessed or opened; 4) digital input to receive a signal when an enclosure containing a flushing mechanism has been accessed or opened; 5) digital input to receive a flush signal from a local switch or a remote terminal unit; 6) at least one analog (4-20 ma) input configured for chlorine residual monitoring (resolution 12 bits); 7) at least one analog (4-20 ma) input for turbidity monitoring; 8) at least one analog (4-20 ma) input for the monitoring of pH levels; 9) at least one input in signal communication with a temperature sensor; 10) additional inputs and 11) additional outputs.

In at least one implementation of the technology, the processor 308 can be configured to execute multiple selectable flushing programs. For example, flushing can be scheduled to occur on specific days; flushing can be scheduled to occur at certain times; flushing can be scheduled to occur for a specific length of time. Other flushing programs 316 are possible within the technology.

The processor 308 can be further configured to execute one or more flushing programs calibrated to a pre-set chlorine (or other disinfectant) residual level sampled by the sampler 310. The processor 308 can be configured to activate a flushing mechanism 306 or means according to a Chlorine (or other disinfectant) residual threshold level, according to input analog signal scaling parameters; and according to a pre-determined hysteresis band related to a flush start signal and a flush stop signal correlated to a predetermined sampled disinfectant concentration level.

Within the technology, a 4-20 mA input signal can be provided to the processor to monitor turbidity levels. The processor 308 can be programmed to establish correct scaling of a turbidity signal depending on the means by which turbidity is measured. One or more processors can be configured to execute a flushing program 316 based upon a pre-set turbidity level. The selectable parameters can include a turbidity threshold level, input analog signal scaling parameters and hysteresis band for flush start and flush stop.

According to at least one implementation of the technology, a 4-20 mA input signal can be provided to the processor 308 to monitor pH level and to establish correct scaling of pH signal depending on the means by which pH is determined for the device. Flushing programs based upon a pre-set pH level. Selectable parameters within the system 100 can include: 1) a pH threshold level; 2) input analog signal scaling parameters; 3) a hysteresis band for flush start and stop from set-point. Other selectable parameters are possible within the technology.

According to at least one implementation of the technology, the processor 308 can be configured to execute flushing programs 316 based upon a pre-set water temperature. Selectable water temperature flushing programs can be correlated to water temperature level, input analog signal scaling parameters and a hysteresis band for flush start and flush stop from set temperature point. Other selectable temperature related flushing programs 326 and selectable parameters are possible within the technology.

In at least one implementation of the technology, a controller 304 can be configured to have at least one selectable internet protocol address. Implementations can also be configured to communicate with a remote device 302 according to the file transfer protocol and to communicate via simple mail transfer protocol. Further implementations can be configured according to a network time protocol.

In order to prevent unauthorized access to a flushing system 100 within the technology, the PAWFS 206 can be configured with multiple levels of access to the controller 304. The controller 304 can be configured with at least the following levels or modes of access: A visualization mode in which an operator can view all system values, either remotely or locally, but cannot execute at least one command; a command mode, in which an operator can view all system values and execute commands, either remotely or locally; and an engineer mode, in which an operator can view all values, execute commands, and send applications and programs or applications and programs to the PAWFS 206, or can reconfigure system parameters and system programs, as discussed above, remotely or locally. The ability to reconfigure and reprogram a system within the technology enables a system to be adaptable to changing conditions such as, for example, environmental conditions and legal requirements. For example, if the maximum allowable level of a residual were changed by law, a system within the technology could be reconfigured with flushing programs using the revised standard as a function.

In at least one implementation, a controller 304 can be configured to send an alarm or alert if a flushing system 100 is tampered with or accessed by an unauthorized user. In at least one implementation, a controller 304 can be configured to shut down or power off in the event of an improper access. A controller 304 can be configured to control a water sampling device.

In at least one implementation within the technology, a system controller 304 can be configured to be accessible via the internet or the World Wide Web page access. A system controller 304 can be provided with web-based Uniform Resource Locator links in order to provide access via a web browser. In at least one implementation, the controller 304 is accessible via Modbus-remote terminal communications. Modbus addresses can be accessed remotely, as via a SCADA 102 for instance. Thus, integration with a preexisting SCADA 102 can be achieved.

In at least one implementation within the technology, multiple system controllers (e.g., 304) can be integrated into a larger overall system. Software, executed remotely or via controllers (e.g., 304) in signal communication with each other, can enable integration and data access to multiple controllers (e.g., 304). Data from controllers (e.g., 304) can be stored in one or more databases for retrieval, display and analysis.

Implementations of the technology can include the following web pages to display system information: An 'index page,' or 'landing page,' displaying relevant contact information and navigation links to other web pages, which may be embedded web pages; an operation overview display, which can display a chronological summary of changes in 'on' and 'off' status of one or more flushing solenoids or other flushing means, a current status of a flushing mechanism, a selector for automatic or manual flushing, a selector for opening or closing a flushing solenoid (if manual flushing has been selected), and a graph depicting 'on/off' operation of a flushing solenoid; an alarms display page, which displays information pertaining to any alarm conditions that are active within a unit, as well as an historical summary of previous alarms.

Figure 4:
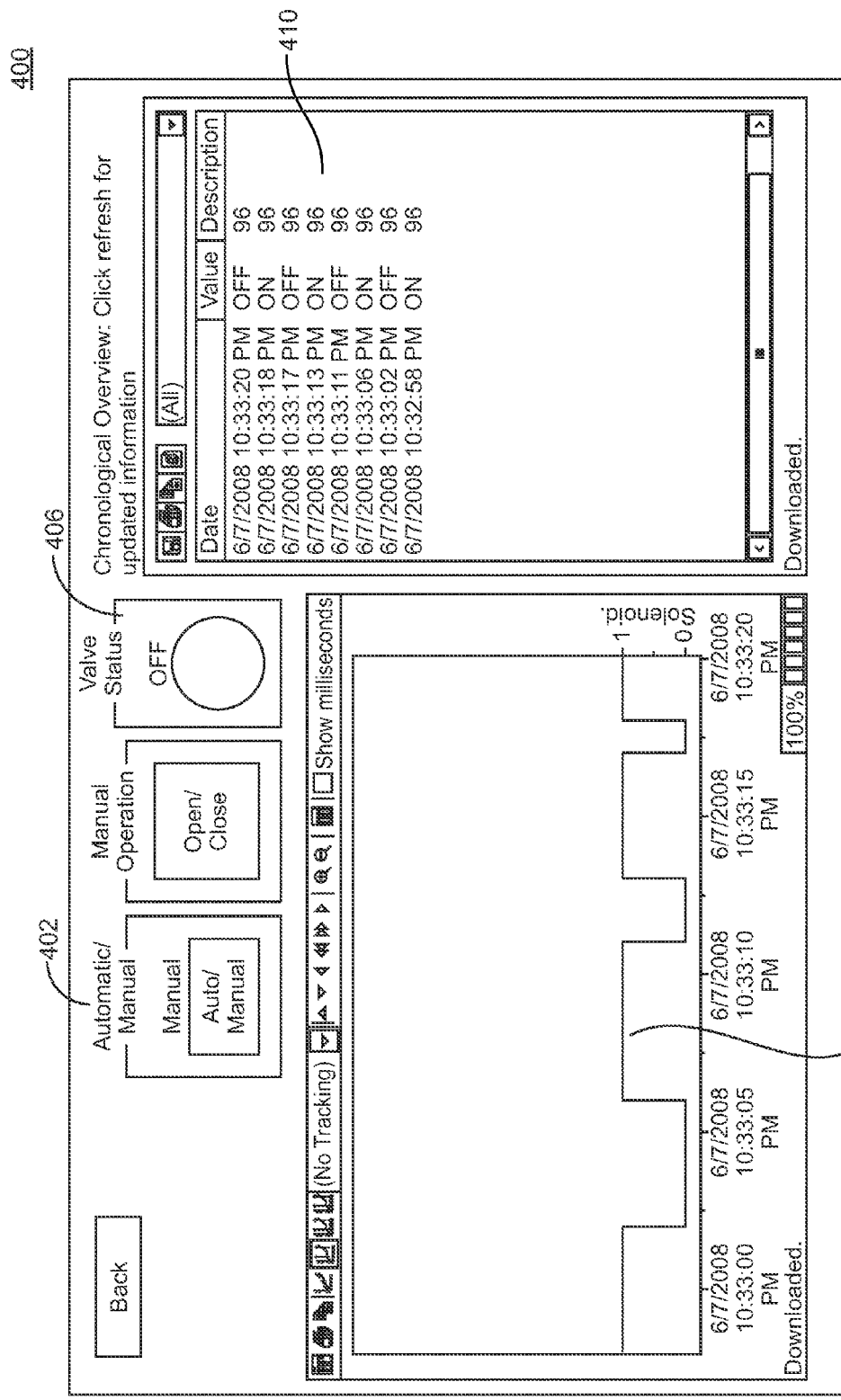
FIG. 4 illustrates an operational status window within the technology.

FIG. 4 illustrates an example operational status window 400 as set forth above. Valve operation selector 402 enables toggling of a flushing system 100 between manual and automatic modes. Selector 404 enables a user to input a command to open or close a flushing valve at a monitoring station 100. Status indicator 406 provides an indication of whether a valve is open or closed or on or off. Trend display 408 tracks when a valve has been opened or closed, and for how long. A chronological overview 410 of flushing operations is illustrated indicating times of valve operations.

Implementations of the technology can also include at least one program operation web page, which can display an overview of selectable flushing programs for a controller. A program operation page or display can indicate if a program is enabled or disabled, and provide for selection of a program by day or week operation, program start time and flushing program duration.

Figure 5:
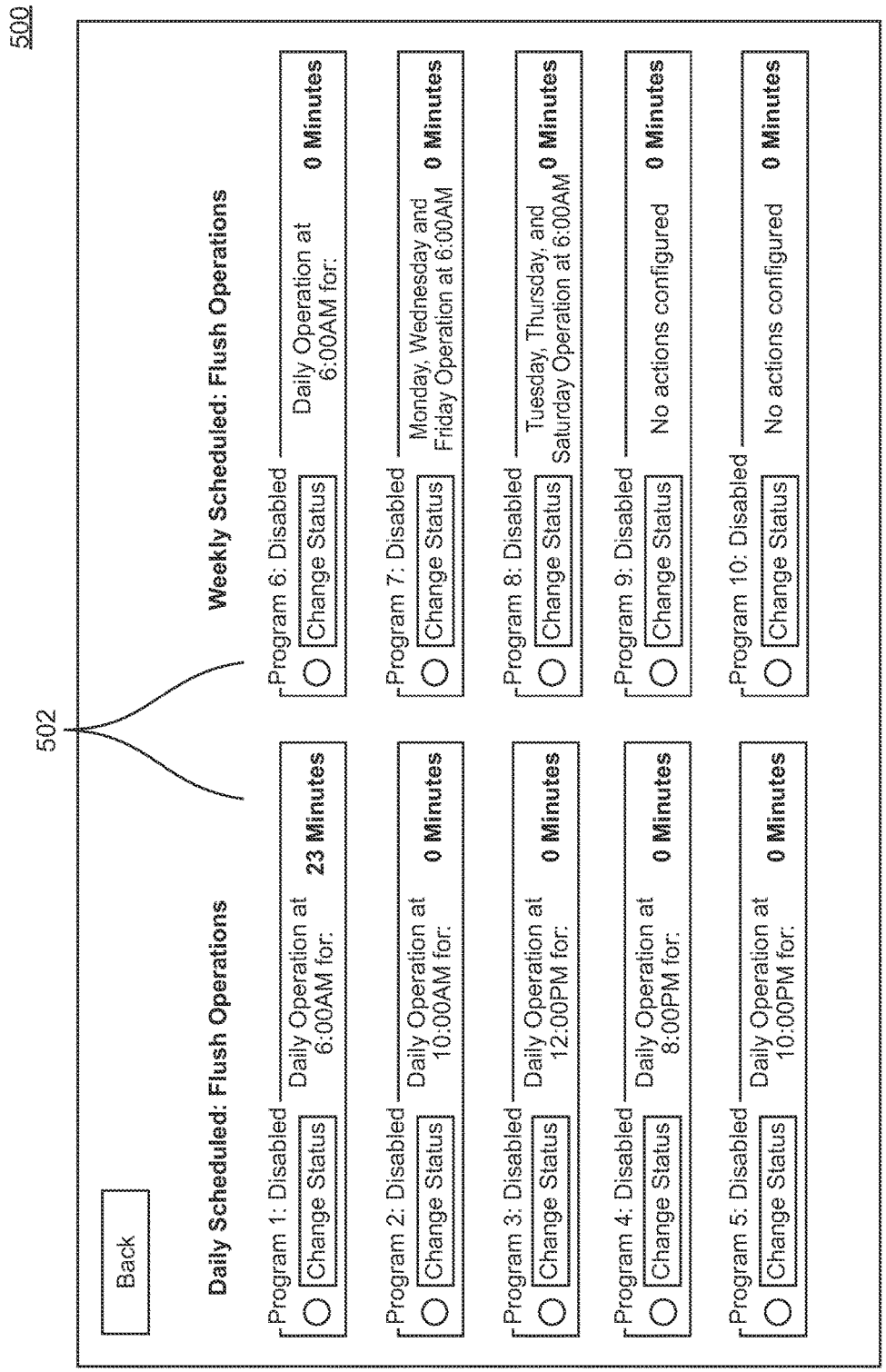
FIG. 5 illustrates a operation configuration and status window within the technology.

FIG. 5 illustrates an example program operation web page 500 (or window). The window 500 shown in FIG. 5 depicts ten selectable flush programs, as described above.

Implementations of the technology can also include a chlorine level page, which can display a trend of residual levels of chlorine versus time based on a sampling period of data collection. Further implementations can also include a turbidity level page which can display a trend of turbidity versus time based on sampling period of data collection. Further implementations of the technology can include a pH level display, which is configured to display a trend chart for pH level versus time based on sampling period of data collection. Further implementations of the technology can comprise a water temperature display, which can display a trend of water temperature versus time based on sampling period of data collection.

Figure 6:
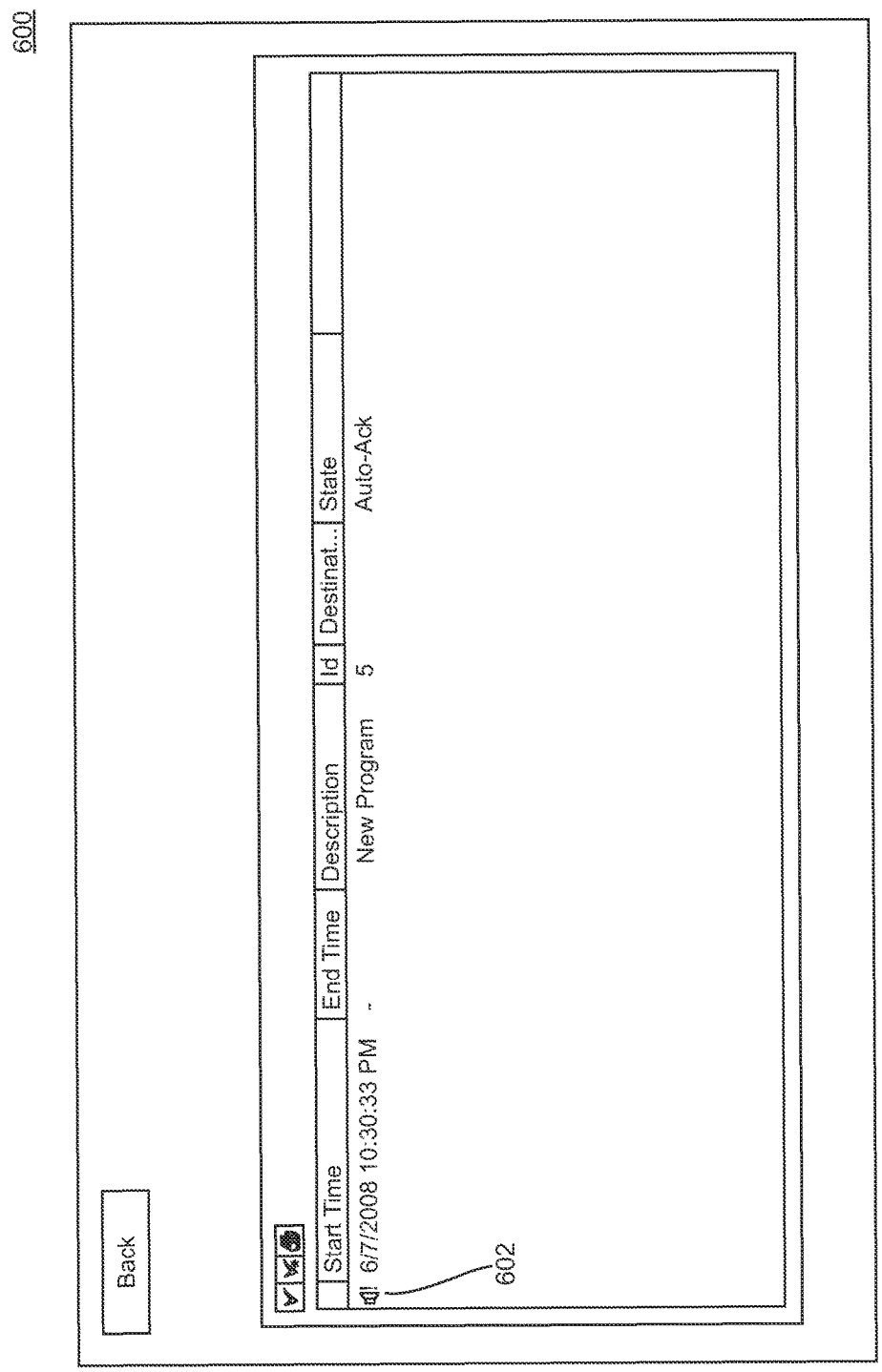
FIG. 6 illustrates an alarm status window within the technology.

FIG. 6 illustrates an implementation of an alarm status page 600 within the technology. An alarm status indicator 602 provides alarm data for a system 100.

Figure 7:
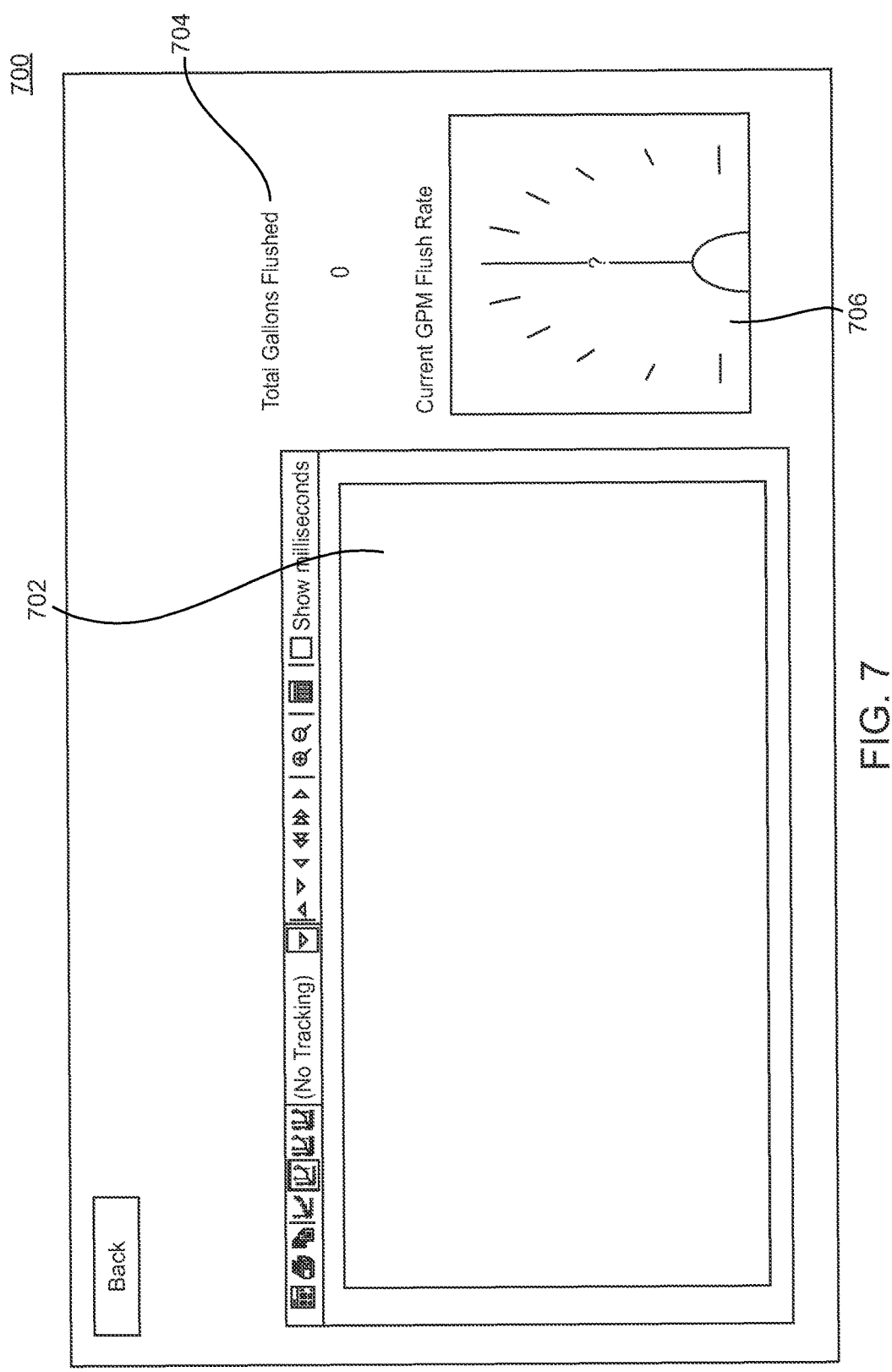
FIG. 7 illustrates flow status window within the technology.

FIG. 7 illustrates a water flow page 700. Flow indicator window 702 can be configured to display flow data collected by a flow meter within the technology. Indicator 704 provides data concerning the total quantity of water flushed by a system within a selectable period of time. Flush rate indicator 706 displays a flow rate. In the example shown rate is expressed in gallons per minute, though other expressions are possible within the technology, for example liters per minute.

Figure 8:
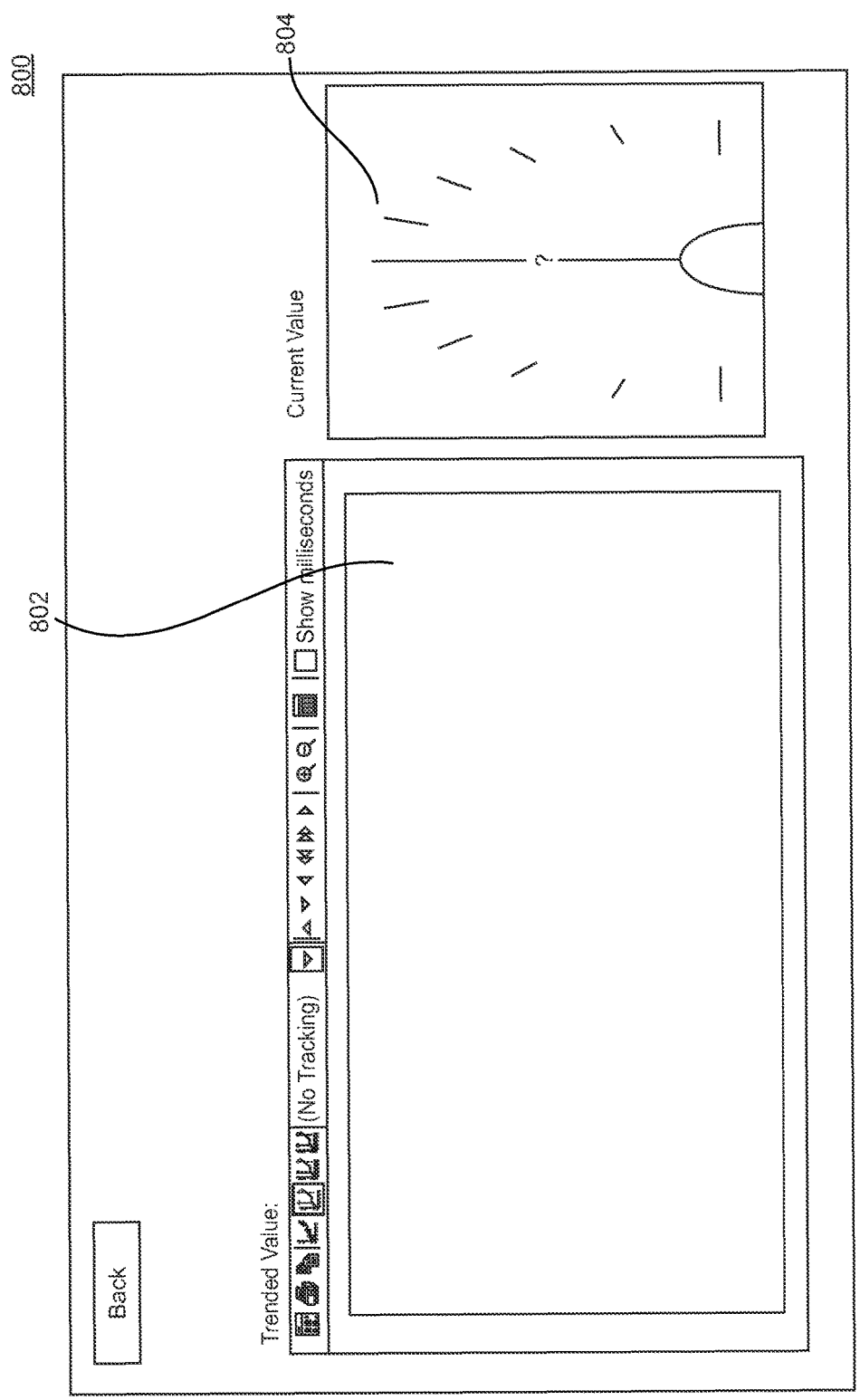
FIG. 8 illustrates a chlorine residual level monitoring window within the technology.

FIG. 8 illustrates a chlorine level trending page 800. Trending window 802 can depict past chlorine levels for a particular system 100. Current value indicator 804 can provide a real time indication of chlorine levels at a particular sampling point.

In at least one implementation of the technology, a web page can be provided which displays the status of one or more controllers. Controller status can comprise pertinent data about the operation and configuration of individual controllers.

In at least one implementation, a parameter setting web page can be provided to enable selection of high and low scaling values for disinfectant residual levels, pH levels, turbidity levels, and temperature levels, in addition to hysteresis settings and values.

Thus, a PAWFS 206 allows for two way communication and remote flushing unit 100 management through a secure web access point or a secure interface in signal communication with a supervisory control and data acquisition system. The PAWFS 206 can be configured to provide and log real time data to an operator. The PAWFS 206 can be integrated with exterior water management devices, such as a SCADA system 202. The PAWFS 206 can be configurable to cause flushing of poor water quality areas when disinfectant residual falls below selectable parameters and under other selectable conditions. Furthermore, the PAWFS 206 can be programmed to flush or clear liquids in accordance with at least one time-based function.

It will be understood that the various windows and pages described above and illustrated in the Figures provide interfaces through which a remote operator can monitor and direct the flushing and sampling operations of a system 100. The windows and pages further enable operators to reset and reconfigure flushing and sampling operations and parameters, thereby reducing the need for manual operations.

Figure 9:
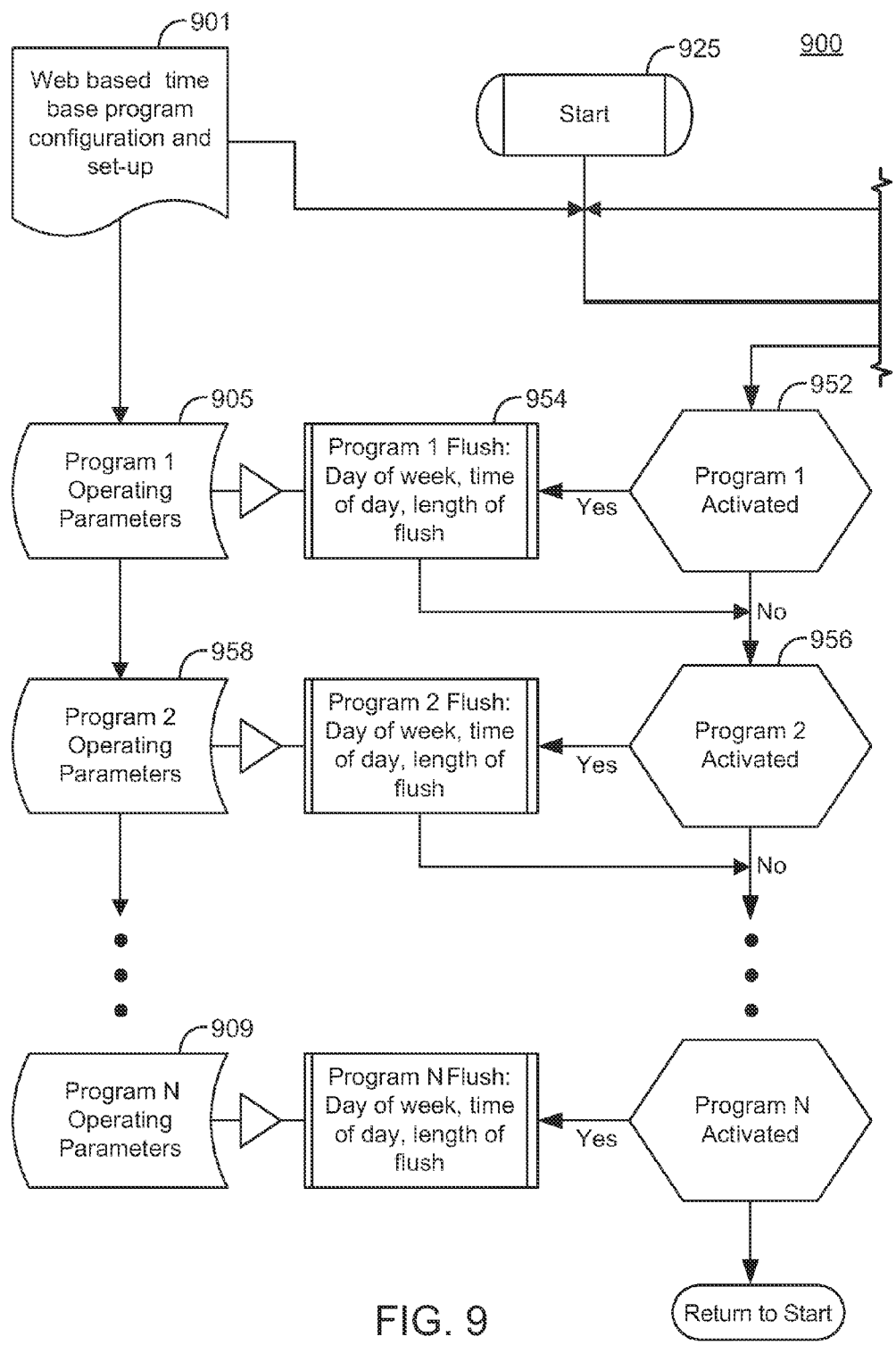
FIG. 9 illustrates an implementation of a method within the technology.

FIG. 9 illustrates an example method 900 within the technology. The illustration depicts that remote configuration of system parameters is enabled throughout the execution of the method. For example, remote configuration 901 of multiple program parameters 905, 958, 909 is possible. Further, remote configuration 902 of various flushing parameters such residual levels 910, turbidity levels 912 and pH levels 914. As discussed above, other configuration settings are possible within the technology. Once the system is started 925, various steps or sequences can occur in parallel, for example flushing actions 920, data collection 922, alarm sequences 924, communication sequences 926 and data display 928. When a series of steps is completed, as will be explained below, the system can return to the start 925 and the sequences can be performed again. Thus water quality data is continually updated and water quality within a system can be maintained. At 940 the system checks to see if a command to flush based on a residual level has been activated. If yes, the system will flush 942 if necessary in accordance with the parameters 910 selected by the operator. The system then checks if a command to flush based on turbidity 944 has been selected. If a command to flush based on turbidity 944 has been selected, the system will flush 946 if necessary according to the turbidity settings 912 imposed by an operator. The system will then determine whether a command to flush based on pH level 948 has been selected. If so, the system will flush 950 if required by the pH settings 914 programmed by an operator. The system then moves on to 952 where it checks whether Program 1 has been activated. If 'Program 1' has been activated the system will flush 954 if required to do so by the settings 905 set by an operator. The system will then move on to 'Program 2' 956 and so on through each program, flushing the system when required by and in accordance with the settings (e.g., 958) as programmed by an operator or pre-installed. Once all programs (e.g., 952, 956) have been cycled the system returns to start 925. In parallel with the flushing actions 920, the system also collects data 922. At 960 the system checks to determine whether flushing solenoid has been changed from an 'off' setting to an 'on' setting and whether the flushing solenoid has been changed from an 'on' setting to an 'off' setting. If a setting change has occurred, the system will log the time and date of the change. After a predetermined amount of time has elapsed 968, for example 30 minutes, the system can log the value of a residual level 970 for a water sample, log the value of turbidity level 972 for a water sample, log the value of the level 974 for a water sample and log a temperature value for a water sample (not shown). Other log settings are possible within the technology.

Also in parallel with the flushing actions 920 and data collection 922 the system can check alarm settings and values 924. The system can check to see if any alarms have been triggered 976, for example, if a flushing station has been accessed by an unauthorized actor. If an alarm has been triggered, the system can log the alarm. The system can be configured to then send an alarm notification to a remote location for review by an operator.

Throughout the parallel systems described above, communications 926 with one or more remote locations are possible. The system can respond to any data requests via a RS485 port, via an Ethernet connection 984 or via a GSM or GPRS port. As discussed above, communications with remote and/or local locations and operators is possible via other electronic means. The system provides information on one or more displays, which can be internet displays 928. As discussed above, the technology can display system operational status 988 for a flushing/sampling station, and residual level data 990, including historical trends and data logging. The technology can display turbidity information 992, pH information 994, other system information, including current and past system parameters and settings 996, and navigation and contact information 998 for a system. The display data can be combined with display data from multiple stations.

A station within the technology can include a flow controlled passage for pressurized water having an inlet adapted for fluid connection to a subterranean pressurized water distribution system, the flow controlled passage having a conduit for directing pressurized water received in the inlet to an above ground routing conduit for redirecting pressurized water. The technology can include a flow control valve disposed along a flow controlled passage for permitting and prohibiting the flow of pressurized water through the flow controlled passage, a memory, a water sampling apparatus connected to a water source, and a controller in signal communication with said flow control valve. The technology can include a processor in signal communication with the water sampling apparatus and the controller. The processor can be configured to execute a flushing program stored in memory. The processor can be configured to actuate the controller according to various flushing programs, whereby the controller is enabled to control the flow of pressurized water by activating and deactivating the flow control valve. Implementations of the technology include an interface in signal communication with the processor whereby an operator can input instructions to the processor or the memory or both.

In at least one implementation of the technology, the processor can be configured to receive water sampling data from the water sampling apparatus and store the water sampling data in memory. A sampling apparatus can be controlled by a controller in accordance with commands or instructions from the processor.

In at least one implementation of the technology, the processor can be configured to transmit water sampling data to at least one remote device or remote location.

As discussed above, sampled water data can include disinfectant residual level data, pH level data, turbidity level data and temperature data.

The implementations, examples and descriptions set forth above should in no way be considered as limiting the subject matter of the following claims.

What is claimed is:

1. A method of maintaining water quality in a water distribution system using a flushing and sampling station, comprising:

flushing the water distribution system in accordance with a residual flush program stored in a memory of the flushing and sampling station, the residual flush program configured to activate a flushing mechanism comprising a flow control valve in fluid connection to the water distribution system, activation of the flushing mechanism comprising opening and closing the flow control valve in response to a comparison between a sampled residual level value and a residual set point level according to a pre-determined hysteresis band related to a flush start signal and a flush stop signal correlated to the residual set point level;

flushing the water distribution system in accordance with a turbidity flush program stored in the memory of the flushing and sampling station, the turbidity flush program configured to activate the flushing mechanism by opening and closing the flow control valve in response to a comparison between a sampled turbidity level value and a turbidity set point level according to a pre-determined hysteresis band related to a flush start signal and a flush stop signal correlated to the turbidity set point level;

flushing the water distribution system in accordance with a pH flush program stored in the memory of the flushing and sampling station, the pH flush program configured to activate the flushing mechanism by opening and closing the flow control valve in response to a comparison between a sampled pH level value and a pH set point level according to a pre-determined hysteresis band related to a flush start signal and a flush stop signal correlated to the pH set point level; and flushing the water distribution system in accordance with a time-based flushing program stored in the memory of the flushing and sampling station, the time-based flushing program configured to activate the flushing mechanism by opening and closing the control valve based on at least one program parameter when it is determined that the time-based flushing program is active.

2. The method of claim 1, further comprising:
setting the residual set point level, the turbidity set point level, and the pH set point level by an operator of the flushing and sampling station.

3. The method of claim 1, wherein the flushing and sampling station further comprises:
a flow controlled passage for pressurized water having an inlet adapted for fluid connection to the water distribution system, the flow controlled passage having a conduit for directing pressurized water received in the inlet to an above ground routing conduit for redirecting the pressurized water;
the flow control valve disposed along the flow controlled passage for enabling the flushing of the water distribution system by permitting and prohibiting the flow of pressurized water through the flow controlled passage; and
a water sampling apparatus for obtaining water sample data corresponding to a sample of the pressurized water from the flow controlled passage.

4. The method of claim 3, further comprising:
determining a state change of the flow control valve of the flushing and sampling station; and
logging a time and date of the state change of the flow control valve.

5. The method of claim 4, further comprising:
logging the residual level value of water in the water distribution system; logging the turbidity level value of water in the water distribution system; logging the pH level value of water in the water distribution system; and
logging a temperature level value of water in the water distribution system.

6. The method of claim 5, wherein at least one of logging the residual level value, logging the turbidity level value, logging the pH level value, and logging the temperature value occurs a predetermined time after determining a state change of the flow control valve.

7. The method of claim 1, further comprising:
determining whether an alarm has been triggered;
logging a time of the alarm when it is determined that the alarm has been triggered; and
sending an alarm notification to an operator of the flushing and sampling station when it is determined that the alarm has been triggered.

8. The method of claim 1, further comprising:
communicating with a remote location by responding to a data request from the remote location.

9. The method of claim 1, further comprising:
displaying an operational status of the flushing and sampling station, the operational status including at least one of turbidity information, pH information, historical trend information, and data logging information.

10. A method of maintaining water quality in a water distribution system including:
providing a flow controlled passage for pressurized water having an inlet adapted for fluid connection to a subterranean pressurized water distribution system, the flow controlled passage having a conduit for directing pressurized water received in the inlet to an above ground routing conduit for redirecting the pressurized water;

providing a flow control valve disposed along the flow controlled passage for permitting and prohibiting the flow of pressurized water through the flow controlled passage;
providing a memory;
providing a water sampling device connected to a water source;
placing a controller in signal communication with the flow control valve; and
placing a processor in signal communication with the water sampling device and the controller, and executing flushing programs stored in the memory, at least one of the flushing programs configured to cause the controller to open and close the flow control valve in response to a comparison between a current water property value from the water sampling device and a set point level for the water property according to a pre-determined hysteresis band related to a flush start signal and a flush stop signal correlated to the set point level; and
inputting instructions to the processor via at least one interface in signal communication with the processor for execution by the processor.

11. The method of claim 10, further comprising:
receiving water sampling data from the water sampling device;
storing the water sampling data in the memory; and
transmitting the water sampling data to at least one remote device.

12. The method of claim 11, wherein the water sampling data includes the current water property value.

13. The method of claim 10, wherein the water property comprises one of disinfectant residual, pH, turbidity, and temperature.

14. The method of claim 10, wherein the interface is a web page.

15. The method of claim 10, wherein the interface is a SCADA system.

16. A method of maintaining water quality in a water distribution system using a flushing and sampling station, comprising:
flushing the water distribution system in accordance with a plurality of flushing programs stored in a memory of the flushing and sampling station, at least one of the plurality of flushing programs configured to activate a flushing mechanism of the flushing and sampling station, the flushing mechanism comprising a flow control valve in fluid connection to the water distribution system, activation of the flushing mechanism comprising opening and closing the flow control valve in response to a comparison between a sampled water property value determined by the flushing and sampling station and a set point level for the water property according to a pre-determined hysteresis band related to a flush start signal and a flush stop signal correlated to the set point level;
determining whether an alarm has been triggered;
logging a time of the alarm when it is determined that an alarm has been triggered;
determining a state change of the flow control valve of the flushing and sampling station; and
logging a time and date of the state change of the flow control valve when it is determined that a state change of the flow control valve has occurred.

17. The method of claim 16, further comprising:
logging a residual level value of water in the water distribution system;

logging a turbidity level value of water in the water distribution system;

logging a pH level value of water in the water distribution system; and logging a temperature level value of water in the water distribution system.

18. The method of claim 16, further comprising:

sending an alarm notification to an operator of the flushing and sampling station when it is determined that an alarm has been triggered.

19. The method of claim 16, further comprising:

communicating with a remote location by responding to a data request from the remote location; and displaying an operational status of the flushing and sampling station.

20. The method of claim 19, wherein displaying the operation status of the flushing and sampling station further comprises displaying at least one of turbidity information, pH information, historical trend information, and data logging information.

* * * * *